United States Patent [19]

Kadin

[11] 3,998,954
[45] Dec. 21, 1976

[54] 1,3(2H,4H)-DIOXOISOQUINOLINE-4-CARBOXAMIDES USED AS ANTI-INFLAMMATORY AGENTS

[75] Inventor: Saul B. Kadin, New London, Conn.

[73] Assignee: Pfizer Inc., New York, N.Y.

[22] Filed: Mar. 27, 1975

[21] Appl. No.: 562,797

Related U.S. Application Data

[60] Division of Ser. No. 113,082, Feb. 5, 1971, Pat. No. 3,886,163, which is a continuation of Ser. No. 674,664, Oct. 11, 1967, abandoned, which is a continuation-in-part of Ser. No. 649,462, June 28, 1967, abandoned.

[52] U.S. Cl. .......................... 424/258; 424/248.5; 424/250; 424/248.54
[51] Int. Cl.² ........................................ A61K 31/47
[58] Field of Search ................ 424/258, 248, 250; 260/281

[56] References Cited
UNITED STATES PATENTS

| | | | |
|---|---|---|---|
| 3,726,875 | 4/1973 | Kadin | 260/281 |
| 3,886,163 | 5/1975 | Kadin | 260/281 |

*Primary Examiner*—Leonard Schenkman
*Attorney, Agent, or Firm*—Connolly and Hutz

[57] ABSTRACT

1,3(2H,4H)-Dioxoisoquinoline-4-carboxamides, nuclear unsubstituted and substituted, are prepared by reacting the appropriate homophthalimide with potassium cyanate. Secondary carboxamides are prepared by reacting homophthalimide with appropriate isocyanates, and tertiary carboxamides are prepared by aminolysis of 4-carbalkoxy compounds, which are in turn prepared by alcoholysis of the corresponding 4-carboxanilides. Corresponding 5,6,7,8-tetrahydro compounds are similarly prepared. The various 2-substituted homophthalimides are prepared by reacting homophthalic acid with appropriate amine. The 4-carboxamides are anti-inflammatory agents.

8 Claims, No Drawings

1,3(2H,4H)-DIOXOISOQUINOLINE-4-CARBOXAMIDES USED AS ANTI-INFLAMMATORY AGENTS

CROSS REFERENCE TO RELATED APPLICATIONS

This application is a division of application Ser. No. 113,082 filed Feb. 5, 1971 now U.S. Pat. No. 3,886,163 which is a continuation of application Ser. No. 674,664 filed Oct. 11, 1967 now abandoned which is a continuation in part of application Ser. No. 649,462 filed June 28, 1967 and now abandoned.

BACKGROUND OF THE INVENTION

This invention relates to a series of novel chemotherapeutic agents and a process for the preparation thereof; in particular, it relates to 1,3(2H,4H)-dioxoisoquinoline-4-carboxamides.

The prior art teaches that primary and secondary carboxamide groups can be substituted for an active hydrogen atom by reacting isocyanic acid or appropriate isocyanate with an organic molecule containing the active hydrogen.

However, this process is not suitable for the preparation of tertiary carboxamides. For this reason, it was desired that 1,3(2H,4H)-dioxoisoquinoline-4-carbalkoxy compounds be prepared, since aminolysis of the esters with appropriate secondary amine would provide a facile synthesis of tertiary carboxamides of the instant invention. Unexpectedly, treating homophthalimide with ethyl chloroformate under basic conditions, usually a satisfactory procedure for generating a carbethoxy derivative, resulted in an unsatisfactory yield of the desired product.

The prior art also teaches that treating an amide with alcohol is usually a poor method of preparing the corresponding ester. One skilled in the art would expect the interconversion between ester and carboxamide to favor the formation of the carboxamide at the expense of the ester.

SUMMARY OF THE INVENTION

The novel carboxamides of this invention are represented by the formulae

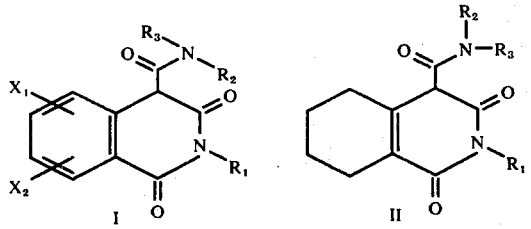

wherein:

$R_1$ is selected from the group consisting of hydrogen; alkyl containing up to 6 carbon atoms; alkenyl containing up to 6 carbon atoms; cycloalkyl containing up to 6 carbon atoms; methoxy; hydroxy; benzyloxy; propargyl; 2-furyl; furfuryl; 2-tetrahydrofuryl; tetrahydrofurfuryl; phenyl with up to one substituent selected from the group consisting of fluorine, chlorine, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy; and benzyl with up to one nuclear substituent selected from the group consisting of fluorine, chloride, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy;

$R_2$ is selected from the group consisting of hydrogen; primary and secondary alkyl containing up to 6 carbon atoms; primary and secondary alkenyl containing up to 6 carbon atoms; primary and secondary alkynyl containing from 3 up to 6 carbon atoms; and alkoxyethyl containing up to 4 carbon atoms;

$R_3$ is selected from the group consisting of hydrogen; alkyl containing up to 6 carbon atoms; alkenyl containing up to 6 carbon atoms; alkynyl containing from 3 up to 6 carbon atoms; cycloalkyl containing up to 6 carbon atoms; carbalkoxyalkyl containing up to 5 carbon atoms; polyfluoroalkyl containing up to 3 carbon atoms, acyl containing up to 4 carbon atoms; benzoyl; tetrahydrofurfuryl; adamantyl; pyridyl; phenyl containing up to 2 substituents each selected from the group consisting of fluorine, chlorine, bromine, alkoxy containing up to 2 carbon atoms, alkyl containing up to 3 carbon atoms, acetyl, trifluoromethyl, nitro, amino, methylsulfonyl, trifluoromethylsulfonyl, dimethylsulfonamido, acetamido and hydroxy; naphthyl with up to 1 substituent consisting of fluorine, chlorine, bromine, alkoxy containing up to 2 carbons atoms, alkyl containing up to 3 carbon atoms, acetyl, trifluoromethyl, nitro, amino, methylsulfonyl, trifluoromethylsulfonyl, dimethylsulfonamido, acetamido and hydroxy; and aralkyl containing up to 8 carbon atoms with up to 1 nuclear substituent selected from the group consisting of fluorine, chlorine, bromine, alkoxy containing up to 2 carbon atoms, alkyl containing up to 3 carbon atoms, acetyl, trifluoromethyl, nitro, amino, methylsulfonyl, trifluoromethylsulfonyl, dimethylsulfonamido, acetamido and hydroxy; and $R_2$ and $R_3$, taken together, form a heterocycle selected from the group consisting of pyrrolidine, piperidine, hexamethyleneimine, morpholine, piperazine, N-methylpiperazine and N-phenylpiperazine;

provided that $R_2$ is always hydrogen when $R_3$ is selected from the group consisting of tertiary alkyl, tertiary alkenyl, tertiary alkynyl, nitro-substituted phenyl, nitro-substituted aralkyl, and acyl; and $X_1$ and $X_2$ are each selected from the group consisting of hydrogen, fluorine, chlorine, bromine, alkoxy containing up to 2 carbon atoms, alkyl containing up to 3 carbon atoms, acetyl, trifluoromethyl, nitro, amino, methylsulfonyl, trifluoromethylsulfonyl, dimethylsulfonamido, acetamido and hydroxy.

Compounds of particular interest are those of formula I wherein $R_1$ is hydrogen or methyl, $R_2$ is hydrogen, $R_3$ is phenyl with up to two substituents each selected from the group consisting of fluorine, chlorine, bromine, alkoxy containing up to 2 carbon atoms, alkyl containing up to 3 carbon atoms, acetyl, trifluoromethyl, nitro, amino, methylsulfonyl, trifluoromethylsulfonyl, dimethylsulfonamido, acetamido and hydroxy, and $X_1$ and $X_2$ are each hydrogen.

Useful as intermediates in the preparation of the carboxamides of the instant invention are the novel homophthalimides of the formula

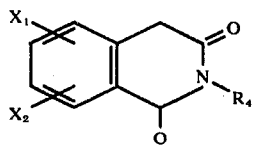

wherein $X_1$ and $X_2$ are as aforesaid and $R_4$ is selected from the group consisting of alkyl containing between 2 and 6 carbon atoms; alkenyl containing up to 6 carbon atoms; cycloalkyl containing up to 6 carbon atoms; methoxy; propargyl; 2-furyl; furfuryl; 2-tetrahydrofuryl; tetrahydrofurfuryl; phenyl with one substituent selected from the group consisting of fluorine, chlorine, bromine alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy; and benzyl with one nuclear substituent selected from the group consisting of fluorine, chlorine, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy.

Certain of the hereinbefore specified carboxamides, particularly those wherein $R_2$ is other than hydrogen, are most easily prepared by aminolysis of novel 4-carbalkoxy compounds of the formula

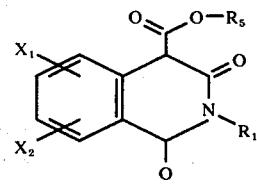

wherein $R_1$ is selected from the group consisting of hydrogen; alkyl containing up to 6 carbon atoms; alkenyl containing up to 6 carbon atoms; cycloalkyl containing up to 6 carbon atoms; methoxy; hydroxy; benzyloxy; propargyl; 2-furyl; furfuryl; 2-tetrahydrofuryl; tetrahydrofurfuryl; phenyl with up to one substituent selected from the group consisting of fluorine, chlorine, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy; and benzyl with up to one nuclear substitutent selected from the group consisting of fluorine, chlorine, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy; $R_5$ is alkyl containing up to 6 carbon atoms; and $X_1$ and $X_2$ are each selected from the group consisting of hydrogen, fluorine, chlorine, bromine, alkoxy containing up to 2 carbon atoms, alkyl containing up to 3 carbon atoms, acetal, trifluoromethyl, nitro, amino, methylsulfonyl, trifluoromethylsulfonyl, dimethylsulfonamido, acetamido and hydroxy.

However, attempts to synthesize said carbalkoxy compounds by conventional methods have resulted in unsatisfactory procedures. A surprisingly satisfactory process is achieved by alcoholysis of hereinbefore specified carboxamides wherein $R_1$ is selected from the group consisting of hydrogen; alkyl containing up to 6 carbon atoms; alkenyl containing up to 6 carbon atoms; cycloalkyl containing up to 6 carbon atoms; methoxy; hydroxy; benzyloxy; propargyl; 2-furyl; furfuryl; 2-tetrahydrofuryl; tetrahydrofurfuryl; phenyl with up to one substituent selected from the group consisting of fluorine, chlorine, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy; and benzyl with up to one nuclear substituent selected from the group consisting of fluorine, chlorine, bromine, alkoxy containing up to 2 carbon atoms, alkyl containing up to 3 carbon atoms, trifluoromethyl, nitro, amino, methylsulfonyl, trifluoromethylsulfonyl, dimethylsulfonamido, acetamido and hydroxy; $R_2$ is hydrogen; and $R_3$ is phenyl with up to two substituents each selected from the group consisting of fluorine, chlorine, bromine, alkoxy containing up to 2 carbon atoms, alkyl containing up to 3 carbon atoms, acetyl, trifluoromethyl, nitro, amino, methylsulfonyl, trifluoromethylsulfonyl, dimethylsulfonamido, acetamido and hydroxy. Thus, the carboxanilides of the instant invention are useful as synthetic intermediates in the preparation of other useful compounds.

The novel 5, 6, 7, 8-tetrahydro-1,3-(2H,4H)-dioxoisoquinoline-4-carboxamides of formula II are prepared in the same manner as are the corresponding unsubstituted compounds of formula I, using the appropriate tetrahydro substrates.

The novel carboxamides of the instant invention are useful as anti-inflammatory agents.

DETAILED DESCRIPTION OF THE INVENTION

The novel carboxamides of the instant invention are prepared by several methods, with the particular method used depending upon whether the carboxamide is primary ($R_2$=$R_3$=H), secondary ($R_3 \neq R_2$=H) or tertiary ($R_2$ and $R_3 \neq$H). However, each procedure uses an appropriate isoquinoline-1,3(2H,4H)-dione (homophthalimide) as common substrate. Of all the homophthalimides, within the scope of the instant invention, only the 2unsubstituted, 2-methyl, 2-phenyl, 2-hydroxy, 2-benzyloxy and 2-benzyl substituted compounds are known. The novel 2-substituted homophthalimides, represented by the formula

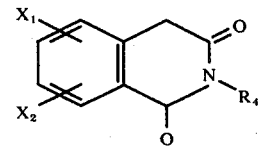

wherein $X_1$, $X_2$ and $R_4$ are as aforesaid, are most easily prepared by treating a homophthalic acid with an amine of the formula $R_4$—$NH_2$. Amines $R_4$—$NH_2$, in turn, are either known compounds or can be readily synthesized by methods familiar to those skilled in the art. It is preferable to use at least a molar equivalent amount of said amine in the reaction with homophthalic acid, and often an excess amount is beneficial. The process of mixing the two materials is usually exothermic, but additional heat is necessary to produce the imide. Heating the mixture with an oil bath to about 175°–275° C. for up to two hours will accomplish the desired condensation although the reaction with certain amines has been effected in as little as 40 minutes. Water is produced as a by-product of the condenstion but is driven off by the high reaction temperature. The desired product can be isolated in a variety of ways known to those skilled in the art. For example, the reaction mixture can be poured while hot into an excess of alcohol, which is then concentrated and cooled to cause crystallization of product. Also, the reaction mixture can be allowed to cool and solidify, with the product then isolated by crystallization.

The corresponding 5,6,7,8-tetrahydro-1,3(2H,4H)-dioxoisoquinolines of the formula

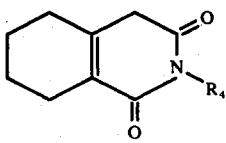

wherein $R_4$ is as aforesaid, are similarly prepared and are used in the preparation of tetrahydrocarboxamides of formula II in a manner analogous to hereinafter discussed conversion of homophthalimides to carboxamides of formula I.

The various primary carboxamides, wherein $R_2$ and $R_3$ are each hydrogen, are prepared by treating aforesaid homophthalimides with inorganic cyanates such as potassium cyanate. The reaction is conducted in a reaction-inert solvent. It may be desirable to dissolve each of the two substrate materials first and then to combine the two solutions to effect the reaction; it is not necessary that the same solvent be used for each substrate so long as the solvents are mutually miscible. Thus, the cyanate salt can be dissolved in water and the homophthalimide in dimethylformamide, dimethylsulfoxide, acetone or alcohol. It is desirable to use at least about a molar equivalent amount of cyanate, and best results are often obtained by using an excess of that reagent. The reaction mixture is heated, using a steam bath or other appropriate heat source. Reaction time is not critical but the conversion is usually complete within about 2–4 hours, after which time the product is isolated. A convenient means of isolation is to add the reaction mixture to an excess of acidified ice water, which causes the product to precipitate.

The various primary tetrahydrocarboxamides are prepared by similarly treating the 5,6,7,8-tetrahydro-1,3(2H,4H)-dioxoisoquinolines. In like manner, each of the following synthetic procedures, which are directed to carboxamides of formula I, may be used with a corresponding tetrahydro substrate for the preparation of carboxamides of formula II.

The secondary carboxamides of the instant invention, wherein $R_2$ is hydrogen and $R_3$ is not hydrogen, may be synthesized by treating aforesaid homophthalimides in basic solution with an appropriate isocyanate of the formula $R_3$—NCO wherein $R_3$ corresponds to the nitrogen substituent of the desired carboxamide. Common reaction-inert organic solvents, such as tetrahydrofuran, dimethylformamide and dimethylsulfoxide, are acceptable. It is preferable that a slight molar excess of base, such as triethylamine, be added to the solvent. Many of aforesaid isocyanates $R_3$—NCO are known compounds and the others may be synthesized by methods known to those skilled in the art. It is preferable to use at least about a molar equivalent amount of isocyanate and best results are usually obtained by using an excess. The mixture may be heated to effect the reaction. Although temperatures below that of reflux may be used, they require longer reaction times; at reflux temperature, the reaction may be complete within a time ranging from several minutes up to about 24 hours, depending upon the particular carboxamide being prepared. The product is easily recovered by pouring the reaction mixture into an excess of ice water containing a slight excess of hydrochloric acid; the carboxamide precipitates and is collected by filtration.

The tertiary carboxamides, wherein neither $R_2$ nor $R_3$ is hydrogen, cannot be prepared by the isocyanate procedure since the isocyanate group cannot accommodate a disubstituted nitrogen atom. Therefore, these compounds are conveniently prepared by aminolysis of 4-carbalkoxy compounds with secondary amines of the formula

wherein $R_2$ and $R_3$ correspond to the particular nitrogen substituents of the desired carboxamide. This aminolysis procedure may also be used advantageously to prepare certain of the secondary carboxamides of the instant invention. When synthesis of any of aforesaid isocyanates $R_3$—NCO is inconvenient or difficult, the 4-carbalkoxy compounds may be treated with primary amines of the formula $R_3$—NH$_2$ to produce the secondary carboxamide, thus avoiding the need to synthesize the corresponding isocyanate. For example, a 4-carbalkoxy compound can be treated with adamantylamine to prepare the 4-carboxamide wherein $R_2$ is hydrogen and $R_3$ is the adamantyl moiety. The aminolysis is conducted in a reaction-inert solvent such as xylene, preferably using a slight molar excess of amine with respect to the 4-carbalkoxy compound. The reaction mixture is refluxed for about 0.5–4 hours. A convenient means of isolating the product is to distill off a portion of the solvent; when the temperature of the solvent vapors in the distilling head is within about one or two degrees of the temperature of the reaction mixture, the mixture is allowed to cool and the product precipitates.

Attempts to synthesize aforesaid 4-carbalkoxy compounds by a conventional procedure were not successful. It would normally be expected by one skilled in the art that treating a homophthalimide with ethyl chloroformate and sodium hydride would generate the corresponding 4-carbethoxyhomophthalimide, since these reagents are commonly used to generate a 4-carbethoxy substituent at the site of an active hydrogen atom. In fact, the 4-carbethoxy derivative was only generated with difficulty and in an unsatisfactory yield.

Surprisingly, it has been found that carboxamides of the instant invention wherein $R_2$ is hydrogen and $R_3$ is substituted or unsubstituted phenyl, i.e., 4-carboxanilides, can be refluxed in alcohol to form the corresponding ester of said alcohol in yields in excess of 90%. This effective conversion of a carboxamide to a carbalkoxy compounds is unexpected since, even in the presence of a substantial excess of alcohol, one skilled in the art would normally expect the amide to predominate in the equilibrium existing between ester and carboxamide. For example, S. M. McElvain, *Characterization of Organic Compounds*, rev. ed. (1953), p. 189, teaches that anilides may be recrystallized from alcohol, indicating that conversion of the amide to the ester is not readily achieved. Furthermore, refluxing for 8 hours on ethanolic solution of acetoacetanilide, an anilide structurally similar to the 4-carboxanilides of the instant invention, does not result in the formation of the corresponding ester. However, heating the carboxanilides of the instant invention in an excess of alcohol containing up to 6 carbon atoms at a temperature between about 50° C. and reflux temperature provides an effective and efficient means of preparing the desired ester. The reaction time is not critical, although at least one hour is preferable. Of course, a reaction temperature below that of reflux will require a longer reaction time to accomplish the same degree of conversion as is possible at reflux; therefore, the higher reaction temperature is usually preferred. Although any carboxanilide of the instant invention may be used to produce the desired esters, particularly good results have been observed by using carboxanilides substituted at the ortho composition with groups such as chlorine and methoxy.

It is noted that aforesaid carboxanilides can also be used advantageously in the preparation of other carboxamides, without formation of the esters as an intermediate. Heating molar equivalent amounts of a carboxanilide and a primary or secondary amine in a reaction-inert solvent, such as xylene, results in the substitution of the amine for the aniline moiety. An excess of the amine is often beneficial. Reflux temperature is preferred, although lower temperatures may be used with correspondingly longer reaction times. Upon cooling, the desired product precipitates and is collected by filtration. Treating 2′-chloro-2-methyl-1,3(2H,4H)-dioxoisoquinoline-4-carboxanilide with benzyl amine to obtain the corresponding N-benzyl carboxamide is an illustration of this procedure.

As indicated hereinbefore, the 1,3(2H,4H)-dioxoisoquinoline-4-carboxamides of the instant invention are useful as anti-inflammatory agents. These compounds are of value in alleviating swelling and inflammation which are symptomatic of rheumatism and arthritis and of other disorders which are responsive to treatment with anti-inflammatory agents. Either as individual therapeutic agents or as mixtures of therapeutic agents, they may be administered alone, but are generally administered with a pharmaceutical carrier selected on the basis of the chosen route of administration and standard pharmaceutical practice. For example, they may be administered orally in the form of tablets or capsules containing such excipients as starch, milk sugar or certain types of clay, etc. They may be administered orally in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

The dosage required to reduce inflammation or swelling in arthritic and rheumatic subjects would be determined by the nature and extent of the symptoms. Generally, small doses will be administered initially, with a gradual increase in the dosage until the optimum level is determined. It will generally be found that when the composition is administered orally, larger quantities of the active ingredient will be required to produce the same level as produced by a small quantity administered parenterally. In general, from about 0.02 to about 200 mg. of active ingredient per kilogram of body weight, administered in single or multiple dose units, will effectively reduce inflammation and swelling.

Particularly effective as anti-inflammatory agents are those carboxamides of the instant invention of formula I wherein $R_1$ is selected from the group consisting of hydrogen and methyl, $R_2$ is hydrogen, and $R_3$ is phenyl with up to two substituents each selected from the group consisting of fluorine, chlorine, bromine, alkoxy containing up to 2 carbon atoms, alkyl containing up to 3 carbon atoms, acetyl, trifluoromethyl, nitro, amino, methylsulfonyl, trifluoromethylsulfonyl, dimethylsulfonamido, acetamido and hydroxy, and $X_1$ and $X_2$ are each hydrogen. Among these compounds, 2-methyl-1,3(2H,4H)-dioxoisoquinoline-4-carboxanilide, 4′-chloro-2-methyl-1,3(2H,4H)-dioxoisoquinoline-4-carboxanilide, 4′-chloro-1,3(2H,4H)-dioxoisoquinoline-4-carboxanilide, 4′-fluoro-2-methyl-1,3(2H,4H)-dioxoisoquinoline-4-carboxanilide and 2′,4′-dichloro-2-methyl-1,3(2H,4H)-dioxoisoquinoline-4-carboxanilide are especially preferred.

It is noted that a common characteristic of many anti-inflammatory agents is that they contain an active hydrogen atom. Each of the 4-caroboxamides of the instant invention shares this property and is an effective proton source, with the active hydrogen being located at the 4-position.

A standard procedure for detecting and comparing anti-inflammatory activity of compounds is the carrageenin rat food edema test, whereby unanesthetized adult male albino rats of 150–190 g. body weight are each numbered, weighed and marked with ink on the right lateral malleolus. One hour after administration of the drug by gavage, edema is induced by injection of 0.05 ml. of 1% solution of carrageenin into the plantar tissue of the marked paws. Immediately thereafter, the volume of the injected paw is measured. The increase in volume three hours after the injection of carrageenin constitutes the individual response. Compounds are considered active if the difference in response between a control and the drug being tested is significant. Standard compounds are phenylbutazone at 33 mg/kg and acetylsalicylic acid at 100 mg/kg, both with oral administration.

The following examples are given to more fully illustrate the instant invention. They are not the only possible embodiments of the invention and are not to be considered as a limitation on the scope thereof.

EXAMPLE I 2-(m-Chlorophenyl)isoquinoline-1,3(2H,4H)-dione

A mixture of homophthalic acid (45.0 g., 0.25 mole) and m-chloroaniline (31.8 g., 0.25 mole) was heated by an oil bath to 175°–180° C. for two hours. When removed from the oil bath, the reaction mixture solidified and was recrystallized twice from ethanol/ethyl acetate, giving 2-(m-chlorophenyl)-isoquinoline-1,3(2H,4H)-dione, 36.0 g. (58% yield), m.p. 160°–161° C.

Anal. Calc'd for $C_{15}H_{10}ClNO_2$: C, 66.3; H, 3,68; N, 5.16. Found: C, 65.71; H, 3.79; N, 5.23.

EXAMPLE II

2-Allylisoquinoline-1,3(2H,4H)-dione

A mixture of homophthalic acid (9.0 g., 0.05 mole) and allylamine (2.8 g., 0.05 mole) was heated by an oil bath to 185°–190° C. for 40 minutes. The mixture solidified upon cooling, and was recrystallized twice from isopropanol, giving 2-allylisoquinoline-1,3(2H,4H)-dione, 4.6 g. (46% yield), m.p. 75°–77° C.

Anal. Calc'd for $C_{12}H_{11}O_2N$; C, 71.62; H, 5.51; N, 6.96. Found: C, 71.61; H, 5.57; N, 6.96.

EXAMPLE III

2-Isopropylisoquinoline-1,3(2H,4H)-dione

A mixture of homophthalic acid (90 g., 0.5 mole) and isopropylamine (59 g., 1 mole) was heated by an oil bath to 175°–180° C. for 90 minutes. The hot mixture was then poured into 600 ml. of ethanol, treated with carbon black and filtered. The mixture was concentrated to about 300 ml. and slowly cooled to room temperature. 2-Isopropylisoquinoline-1,3(2H,4H)-dione precipitated and was collected by filtration, 46 g. (45% yield), m.p. 86°–88° C.

Anal. Calc'd for $C_{12}H_{13}O_2N$: C, 70.91; H, 6.45; N, 6.89. Found: C, 70.93; H, 6.43; N, 6.92.

EXAMPLE IV

2-Methoxyisoquinoline:-1,3-(2H,4H)-dione

A mixture of homophthalic acid (9.0 g., 0.05 mole) and methyoxyamine hydrochloride (4.25 g., 0.05 mole) in 125 ml. of xylene was refluxed for 90 minutes, with water collected in Dean Stark trap as it formed. The reaction mixture was cooled and concentrated by vacuum to one half its original volume, then diluted with ethylacetate, washed with water and dried over sodium sulfate. Recrystallization from isopropanol and ethanol, followed by drying at 100° C. for 4 hours yielded pale pink crystals of 2-methoxyisoquinoline-1,3(2H,4H)-dione, m.p. 113°–114° C.

Anal. Calc'd for $C_{10}H_9NO_3$: C, 62.82; H, 4.74; N, 7.33. Found: C, 62.91; H, 4.77; N, 7.16.

EXAMPLE V

The following products are prepared by the procedure of Example I by substituting an appropriate amine in place of said m-chloroaniline:

2-Hexylisoquinoline-1,3(2H,4H)-dione
2-Cyclopropylisoquinoline-1,3(2H,4H)-dione
2-Cyclohexylisoquinoline-1,3(2H,4H)-dione
2-Propargylisoquinoline-1,3(2H,4H)-dione
2-(2'-Furyl)isoquinoline-1,3(2H,4H)-dione
2-(2'-Tetrahydrofuryl)isoquinoline-1,3(2H,4H)-dione
2-Furfurylisoquinoline-1,3(2H,4H)-dione
2-Tetrahydrofurfurylisoquinoline-1,3(2H,4H)-dione
2-(o-Fluorophenyl)isoquinoline-1,3(2H,4H)-dione
2-(p-Bromophenyl)isoquinoline-1,3(2H,4H)-dione
2-(p-Ethoxyphenyl)isoquinoline-1,3(2H,4H)-dione
2-(m-Isopropylphenyl)isoquinoline-1,3(2H,4H)-dione
2-(o-Methylphenyl)isoquinoline-1,3(2H,4H)-dione
2-(m-Trifluoromethylphenyl)isoquinoline-1,3(2H,4H)-dione
2-(m-Nitrophenyl)isoquinoline-1,3(2H,4H)-dione
2-(p-Aminophenyl)isoquinoline-1,3-(2H,4H)-dione
2-(o-Methylsulfonylphenyl)isoquinoline-1,3-(2H,4H)-dione
2-(m-Trifluoromethylsulfonylphenyl)isoquinoline-1,3(2H,4H)-dione
2-(m-Dimethylsulfonamidophenyl)isoquinoline-1,3(2H,4H)-dione
2-(p-Acetamidophenyl)isoquinoline-1,3(2H,4H)-dione
2-(o-Hydroxyphenyl)isoquinoline-1,3(2H,4H)-dione
2-(o-Fluorobenzyl)isoquinoline-1,3(2H,4H)-dione
2-(p-Bromobenzyl)isoquinoline-1,3(2H,4H)-dione
2-(p-Ethoxybenzyl)isoquinoline-1,3(2H,4H)-dione
2-(m-Isopropylbenzyl)isoquinoline-1,3(2H,4H)-dione
2-(o-Methylbenzyl)isoquinoline-1,3(2H,4H)-dione
2-(m-Trifluoromethylbenzyl)isoquinoline-1,3(2H,4H)-dione
2-(m-Nitrobenzyl)isoquinoline-1,3(2H,4H)-dione
2-(p-Aminobenzyl)isoquinoline-1,3(2H,4H)-dione
2-(o-Methylsulfonylbenzyl)isoquinoline-1,3(2H,4H)-dione
2-(m-Trifluoromethylsulfonylbenzyl)isoquinoline-1,3(2H,4H)-dione
2-(m-Dimethylsulfonamidobenzyl)isoquinoline-1,3(2H,4H)-dione
2-(p-Acetamidobenzyl)isoquinoline-1,3(2H,4H)-dione
2-(o-Hydroxybenzyl)isoquinoline-1,3(2H,4H)-dione

EXAMPLE VI 1,3(2H,4H)-Dioxo-2-methylisoquinoline-4-carboxamide

A solution of potassium cyanate (2.84 g., 0.035 mole) in 10 ml. of water was added with stirring, over a 30 minute period, to a solution of 1,3(2H,4H)-dioxo-2-methylisoquinoline (4.4 g., 0.025 mole) in 20 ml. of dimethylformamide which was heated over a steam bath. The resulting solution was heated for an additional two hours and then poured into an excess of ice water containing 10 ml. of 6N hydrochloric acid. The resulting precipitate was filtered, dried and recrystallized from acetonitrile to give white needles of 1,3(2H,4H)-dioxo-2-methylisoquinoline-4-carboxamide, 3.0 g. (56% yield), m.p. 214°–215° C.

Anal. Calc'd for $C_{11}H_{10}N_2O_3$: C, 60.54; H, 4.62; N, 12.84. Found: C, 60.40; H, 4.85; N, 13.08.

EXAMPLE VII 1,3(2H,4H)-Dioxo-2-phenylisoquinoline-4-carboxamide

The procedure of Example VI was repeated, using 1,3(2H,4H)-dioxo-2-phenylisoquinoline in place of said 2-methyl derivative, to prepare 1,3(2H,4H)-dioxo-2-phenylisoquinoline-4-carboxamide, m.p. 192°–194° C.

Anal. Calc'd for $C_{16}H_{12}N_2O_3$: C, 68.56; H, 4.32; N, 10.00. Found: C, 68.32; H, 4.41; N, 10.33.

EXAMPLE VIII

The procedure of Example VI is repeated, using products of Example V in place of said 1,3-(2H,4H)-dioxo-2-methylisoquinoline, to prepare the following compounds:

1,3(2H,4H)-Dioxo-2-hexylisoquinoline-4-carboxamide
1,3(2H,4H)-Dioxo-2-cyclopropylisoquinoline-4-carboxamide
1,3(2H,4H)-Dioxo-2-cyclohexylisoquinoline-4-carboxamide
1,3(2H,4H)-Dioxo-2-propargylisoquinoline-4-carboxamide
1,3(2H,4H)-Dioxo-2-(2'-furyl)isoquinoline-4-carboxamide 1,3(2H,4H)-Dioxo-2-(2'-tetrahydrofuryl)isoquinoline-4-carboxamide
1,3(2H,4H)-Dioxo-2-(furfuryl)isoquinoline-4-carboxamide
1,3(2H,4H)Dioxo-2-(tetrahydrofurfuryl)isoquinoline-4-carboxamide
1,3(2H,4H)-Dioxo-2-methoxyisoquinoline-4-carboxamide
1,3(2H,4H)-Dioxo-2-hydroxyisoquinoline-4-carboxamide
1,3(2H,4H)-Dioxo-2-benzyloxyisoquinoline-4-carboxamide
1,3(2H,4H(-Dioxo-2-(o-fluorophenyl)isoquinoline-4-carboxamide
1,3(2H,4H)-Dioxo-2-(p-bromophenyl)isoquinoline-4-carboxamide
1,3(2H,4H)-Dioxo-2-(p-ethoxyphenyl)isoquinoline-4-carboxamide
1,3(2H,4H)-Dioxo-2-(m-isopropylphenyl)isoquinoline-4-carboxamide
1,3-(2H,4H)-Dioxo-2-(o-methylphenyl)isoquinoline-4-carboxamide
1,3(2H,4H)-Dioxo-2-(m-trifluoromethylphenyl)isoquinoline-4-carboxamide
1,3(2H,4H)-Dioxo-2-(m-nitrophenyl)isoquinoline-4-carboxamide
1,3(2H,4H)-Dioxo-2-(p-aminophenyl)isoquinoline-4-carboxamide
1,3(2H,4H)-Dioxo-2-(o-methylsulfonylphenyl)isoquinoline-4-carboxamide
1,3(2H,4H)-Dioxo-2-(m-trifluoromethylsulfonylphenyl)isoquinoline-4-carboxamide
1,3(2H,4H)-Dioxo-2-(m-dimethylsulfonamidophenyl)isoquinoline-4-carboxamide
1,3(2H,4H)-Dioxo-2-(p-acetamidophenyl)isoquinoline-4-carboxamide
1,3(2H,4H)-Dioxo-2-(o-hydroxyphenyl)isoquinoline-4-carboxamide
1,3(2H,4H)-Dioxo-2-(o-fluorobenzyl)isoquinoline-4-carboxamide
1,3(2H,4H)-Dioxo-2-(p-bromobenzyl)isoquinoline-4-carboxamide
1,3(2H,4H)-Dioxo-2-(p-ethoxybenzyl)isoquinoline-4-carboxamide
1,3(2H,4H)-Dioxo-2-(m-isopropylbenzyl)isoquinoline-4-carboxamide
1,3(2H,4H)-Dioxo-2-(o-methylbenzyl)isoquinoline-4-carboxamide
1,3(2H,4H)-Dioxo-2-(m-trifluoromethylbenzyl)isoquinoline-4-carboxamide
1,3(2H,4H)-Dioxo-2-(m-nitrobenzyl)isoquinoline-4-carboxamide
1,3(2H,4H)-Dioxo-2-(p-aminobenzyl)isoquinoline-4-carboxamide
1,3(2H,4H)-Dioxo-2-o-(methylsulfonylbenzyl)isoquinoline-4-carboxamide
1,3(2H,4H)-Dioxo-2-(m-trifluoromethylsulfonylbenzyl)isoquinoline-4-carboxamide
1,3(2H,4H)-Dioxo-2-(m-dimethylsulfonamidobenzyl)isoquinoline-4-carboxamide
1,3(2H,4H)-Dioxo-2-(p-acetamidobenzyl)isoquinoline-4-carboxamide
1,3(2H,4H)-Dioxo-2-(o-hydroxybenzyl)isoquinoline-4-carboxamide

EXAMPLE IX 1,3(2H,4H)-Dioxoisoquinoline-4-carboxanilide

A solution containing 1,3(2H,4H)-dioxoisoquinoline (4.0 g., 0.025 mole), triethylamine (2.6 g., 0.026 mole) and phenylisocyanate (3.1 g., 0.026 mole), in 100 ml. of tetrahydrofuran was refluxed for 2 hours. The solution was then poured into an excess of ice water containing 5 ml. of hydrochloric acid. The resulting precipitate was collected by filtration, washed with water, dried and recrystallized from acetic acid, to give 1,3(2H,4H)-dioxoisoquinoline-4-carboxanilide, m.p. 249°–250° C. Anal. Calc'd for $C_{16}H_{11}N_2O_3$: C, 68.56; H, 4.32; N, 10.00. Found: C, 68.86; H, 4.37; N, 9.80.

EXAMPLE X

The procedure of Example IX is repeated, using equivalent amounts of appropriately substituted substrates, to produce the following compounds:

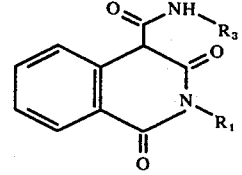

| R₁ | R₃ |
| --- | --- |
| neopentyl | acetyl |
| hydrogen | butyryl |
| phenyl | benzoyl |
| m-trifluoromethylbenzyl | 3-nitronaphthyl |

EXAMPLE XI

The procedure of Example IX was repeated, using appropriately substituted substrates, to produce the following compounds:

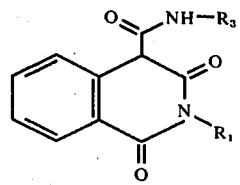

| | | | Anal: Calc'd | | | Found | | |
| --- | --- | --- | --- | --- | --- | --- | --- | --- |
| R₁ | R₃ | M.P., ° C. | C | H | N | C | H | N |
| CH₃ | n-butyl | 176–177 | 65.67 | 6.61 | 10.21 | 65.46 | 6.67 | 10.16 |
| m-chlorophenyl | benzoyl | 201–203 (dec.) | 65.95 | 3.61 | 6.69 | 65.61 | 3.59 | 6.67 |
| CH₃ | carbethoxymethyl | 180–182 | 59.20 | 5.30 | 9.21 | 58.78 | 5.40 | 9.18 |

EXAMPLE XII

The procedure of Example IX was repeated, using appropriately substituted substrates, to produce the following compounds:

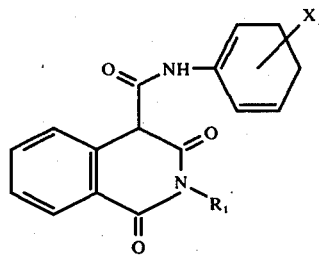

| $R_1$ | X | M.p. °C. | Anal: Calc'd C | H | N | Found C | H | N |
|---|---|---|---|---|---|---|---|---|
| $CH_3$ | H | 246–247 (dec.) | 69.37 | 4.79 | 9.52 | 69.52 | 4.81 | 9.51 |
| $CH_3$ | 2'-Cl | 211–213 (dec.) | 62.10 | 3.98 | 8.52 | 61.99 | 3.97 | 8.47 |
| $CH_3$ | 3'-Cl | 203–205 | 62.10 | 3.98 | 8.52 | 61.82 | 4.05 | 8.64 |
| $CH_3$ | 4'-Cl | 213–214 (dec.) | 62.10 | 3.98 | 8.52 | 62.22 | 3.91 | 8.48 |
| $CH_3$ | 3'-$CH_3$ | 224–225 (dec.) | 70.11 | 5.23 | 9.09 | 69.97 | 5.15 | 9.03 |
| $CH_3$ | 4'-$CH_3$ | 232–234 (dec.) | 70.11 | 5.23 | 9.09 | 69.89 | 5.24 | 9.14 |
| $CH_3$ | 2'-$CH_3$ | 197–198 | 66.65 | 4.97 | 8.64 | 66.69 | 5.02 | 8.74 |
| $CH_3$ | 4'-$OCH_3$ | 222–224 | 66.65 | 4.97 | 8.64 | 66.84 | 5.09 | 8.64 |
| $CH_3$ | 2'-$OC_2H_5$ | 220–221 | 67.44 | 5.36 | 8.28 | 67.74 | 5.14 | 8.33 |
| $CH_3$ | 4'-$OC_2H_5$ | 212–214 | 67.44 | 5.36 | 8.28 | 67.83 | 5.64 | 8.41 |
| m-chlorophenyl | H | 227–229 | 67.61 | 3.84 | 7.17 | 67.66 | 4.08 | 7.11 |
| benzyl | H | 222–223 (dec.) | 74.58 | 4.90 | 7.56 | 74.80 | 4.93 | 7.60 |
| allyl | H | 205–206 | 71.23 | 5.04 | 8.75 | 71.03 | 4.95 | 8.78 |

EXAMPLE XIII

1,3(2H,4H)-Dioxoisoquinoline-4-(N-methyl)carboxamide

To a stirred mixture of 1,3(2H,4H)-dioxoisoquinoline (4.0 g., 0.025 mole) and triethylamine (2.6 g., 0.026 mole) in 10 ml. of dimethylsulfoxide was added dropwise, over a five minute period, a solution of methylisocyanate (1.5 g., 0.026 mole) in 10 ml. of dimethylsulfoxide. After stirring for 2 hours, the solution was poured into an excess of ice water containing 5 ml. of hydrochloric acid. The resulting precipitate was collected by filtration, washed with water, dried and recrystallized from acetonitrile to give 1,3(2H,4H)-dioxoisoquinoline-4-(N-methyl)carboxamide, m.p. 254°–255° C.

Anal. Calc'd for $C_{11}H_{10}N_2O_3$: C, 60.54; H, 4.62; N, 12.84. Found: C, 60.79; H, 4.66; N, 12.56

EXAMPLE XIV

The procedure of Example XIII was repeated, using equivalent amounts of appropriate substrates in place of said isoquinoline and said methylisocyanate, to produce the following compounds:

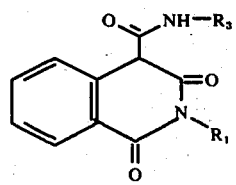

| $R_1$ | $R_3$ | M.p., °C. | Anal: Calc'd C | H | N | Found C | H | N |
|---|---|---|---|---|---|---|---|---|
| H | ethyl | 252–253 (dec.) | 62.06 | 5.21 | 12.07 | 62.34 | 5.13 | 12.08 |
| H | cyclohexyl | 223–225 (dec.) | 67.11 | 6.34 | 9.79 | 67.47 | 6.51 | 10.12 |
| methyl | ethyl | 230–231 | 63.40 | 5.73 | 11.38 | 63.41 | 5.68 | 11.52 |
| methyl | n-propyl | 209–210 | 64.60 | 6.20 | 10.76 | 64.71 | 6.10 | 10.90 |
| methyl | cyclohexyl | 221–223 (dec.) | 67.98 | 6.71 | 9.33 | 68.29 | 6.39 | 9.60 |
| methyl | Methyl | 250–251 (dec.) | 62.06 | 5.21 | 12.07 | 62.29 | 5.13 | 11.87 |
| m-chlorophenyl | ethyl | 211–212 | 63.07 | 4.41 | 8.17 | 62.97 | 4.32 | 8.17 |
| m-chlorophenyl | n-propyl | 195–197 | 63.95 | 4.80 | 7.85 | 64.06 | 4.73 | 7.86 |
| m-chlorophenyl | cyclohexyl | 237–238 (dec.) | 66.58 | 5.33 | 7.06 | 66.85 | 5.51 | 7.39 |
| m-chlorophenyl | carbethoxymethyl | 174–175 | 59.93 | 4.28 | 6.99 | 60.19 | 4.32 | 6.78 |
| isopropyl | ethyl | 173–174 | 65.67 | 6.61 | 10.21 | 65.65 | 6.62 | 10.17 |
| allyl | ethyl | 189–191 | 66.16 | 5.92 | 10.29 | 66.30 | 5.98 | 10.21 |

EXAMPLE XV

The procedure of Example XIII was repeated, using equivalent amounts of appropriate substrates in place of said isoquinoline and said methylisocyanate, to produce the following compounds:

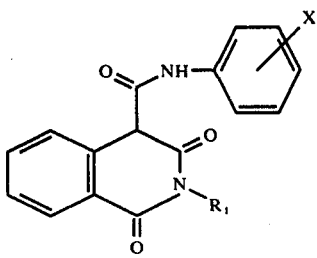

| $R_1$ | X | M.p. ° C. | Anal: Calc'd C | H | N | Found C | H | N |
|---|---|---|---|---|---|---|---|---|
| $CH_3$ | 2'-$CH_3$ | 224–225 (dec.) | 70.11 | 5.23 | 9.09 | 70.45 | 5.19 | 9.17 |
| $CH_3$ | 2',5'-diCl | 222–223 (dec.) | 56.21 | 3.33 | 7.71 | 56.08 | 3.23 | 7.49 |
| H | 2'-Cl | 223–224 (dec.) | 61.06 | 3.52 | 8.90 | 61.47 | 3.15 | 8.99 |
| H | 3'-Cl | 232–234 (dec.) | 61.06 | 3.52 | 8.90 | 60.94 | 3.43 | 9.27 |
| H | 4'-Cl | 243–245 (dec.) | 61.06 | 3.52 | 8.90 | 61.11 | 3.31 | 9.04 |
| H | 2'-$CH_3$ | 242–243 (dec.) | 69.37 | 4.79 | 9.52 | 69.69 | 4.84 | 9.40 |
| H | 3'-$CH_3$ | 232–233 (dec.) | 69.37 | 4.79 | 9.52 | 69.37 | 4.87 | 9.65 |
| H | 4'-$CH_3$ | 236–237 (dec.) | 69.37 | 4.79 | 9.52 | 69.39 | 4.61 | 9.50 |
| H | 2'-$OCH_3$ | 210–211 (dec.) | 65.80 | 4.55 | 9.03 | 66.09 | 4.59 | 9.13 |
| H | 4'-$OCH_3$ | 237–238 (dec.) | 65.80 | 4.55 | 9.03 | 65.96 | 4.48 | 8.92 |
| m-Cl-$C_6H_4$- | 2,5'-diCl | 222–223 (dec.) | 56.21 | 3.33 | 7.71 | 56.08 | 3.23 | 7.49 |
| H | 4'-$OC_2H_5$ | 232–233 (dec.) | 66.65 | 4.97 | 8.64 | 66.57 | 4.92 | 8.86 |
| H | 2'-$OC_2H_5$ | 203–205 (dec.) | 66.65 | 4.97 | 8.64 | 66.29 | 4.92 | 8.86 |

EXAMPLE XVI 1,3(2H,4H)-Dioxo-2-methylisoquinoline-4-(N-benzyl)carboxamide

A mixture of 1,3(2H,4H)-Dioxo-2-methylisoquinoline-4-carbox-o-chloroanilide (8.2 g., 0.025 mole), prepared by the procedure of Example XII, and benzylamine 2.7 g., 0.025 mole) in 100 ml. of xylene was refluxed for 6 hours, after which time the mixture was allowed to cool. The resulting precipitate was collected by filtration, dried and recrystallized from xylene, giving 1,3(2H,4H)-Dioxo-2-methylisoquinoline-4-(N-benzyl)carboxamide, m.p. 171°–173° C. (dec.).

Anal. Calc'd for $C_{18}H_{16}N_2O_3$: C, 70111; H, 5.23; N, 9.09. Found: C, 70.12; H, 5,38; N, 9.37

EXAMPLE XVII

The procedure of Example XVI was repeated, using equivalent amounts of appropriate amines in place of said benzylamine, to produce the following compounds:

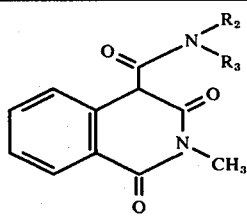

| $R_2$ | $R_3$ | M.p. ° C. | Anal: Calc'd C | H | N | Found C | H | N |
|---|---|---|---|---|---|---|---|---|
| —$(CH_2)_5$— | | 164–165 | 67.11 | 6.34 | 9.79 | 67.15 | 6.27 | 9.84 |
| —$(CH_2)_2$—O—$(CH_2)_2$— | | 160–161 | 62.49 | 5.59 | 9.72 | 62.52 | 5.51 | 9.76 |
| H | allyl | 206–207 | 65.10 | 5.46 | 10.85 | 65.10 | 5.48 | 10.91 |
| H | 4'-$CH_3$O-benzyl | 172–176 (dec.) | 67.44 | 5.36 | 8.28 | 67.75 | 5.60 | 8.52 |
| H | 3',4'-diCl-benzyl | 224–225 | 57.31 | 3.74 | 7.43 | 57.30 | 3.83 | 7.60 |
| H | β-phenethyl | 201–202 | 70.79 | 5.63 | 8.69 | 70.67 | 5.58 | 8.71 |

EXAMPLE XVIII

The procedure of Example XVI was repeated, using equivalent amounts of appropriate amines in place of said benzyl amine, to produce the following compounds:

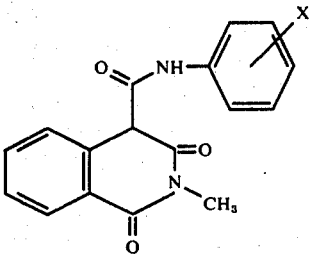

| X | M.p. °C. | Anal: Calc'd C | H | N | Found C | H | N |
|---|---|---|---|---|---|---|---|
| 3',4'-diCH$_3$ | 214–216 (dec.) | 70.79 | 5.63 | 8.69 | 71.06 | 5.77 | 8.83 |
| 3',4'-diCl | 219–220 (dec.) | 56.21 | 3.33 | 7.71 | 56.39 | 3.29 | 7.87 |
| 3'-CF$_3$ | 188–190 (dec.) | 59.67 | 3.62 | 7.73 | 59.76 | 3.68 | 7.52 |
| 2',4'-diOCH$_3$ | 203–204 | 64.40 | 5.12 | 7.91 | 64.40 | 5.15 | 7.84 |
| 2',5'-diOCH$_3$ | 183–184 | 64.40 | 5.12 | 7.91 | 64.45 | 5.11 | 7.84 |

EXAMPLE XIX

Ethyl 1,3(2H,4H)-Dioxo-2-methylisoquinoline-4-carboxylate

A mixture of 1,3(2H,4H)-dioxo-2-methylisoquinoline-4-carbox-o-chloroanilide (16.5 g., 0.05 mole), prepared by the procedure of Example XII, in 125 ml. of absolute ethanol was refluxed for 4 hours. The original white suspension became a clear yellow solution after about 45 minutes, which darkened slightly during the period of additional heating. The solution was then concentrated to one half its original volume and cooled slowly. The resulting precipitate was collected by filtration and dried to give ethyl 1,3(2H,4H)-dioxo-2-methylisoquinoline-4-carboxylate, 11.5 g. (94% yield), m.p. 113°–115° C.

Anal. Calc'd for $C_{13}H_{13}NO_4$: C, 63.15; H, 5.30; N, 5.67. Found: C, 63.07; H, 5.33; N, 5.65.

EXAMPLE XX

Ethyl 1,3(2H,4H)-Dioxoisoquinoline-4-carboxylate

A mixture of 2'-chloro-1,3(2H,4H)-dioxoisoquinoline-4-carboxanilide (67.0 g., 0.25 mole), in one liter of absolute ethanol is refluxed for 5 hours, cooled and filtered. The precipitate is air dried and recrystallized from acetic acid to give ethyl 1,3(2H,4H)-dioxoisoquinoline-4-carboxylate, m.p. 238°–240° C.

Anal. Calc'd. for $C_{12}H_{11}NO_4$: C, 61.80; H, 4.76; N, 6.01. Found: C, 61.51; H, 4.81; N, 6.06.

EXAMPLE XXI

The procedure of Example XIX is repeated, using equivalent amounts of appropriately substituted carboxanilides and appropriate alcohol in place of said carbox-o-chloroanilide and said ethanol, to produce the following compounds:

Methyl 1,3(2H,4H)-Dioxo-2-hexylisoquinoline-4-carboxylate
Methyl 1,3(2H,4H)-Dioxo-2-cyclopropylisoquinoline-4-carboxylate
Methyl 1,3(2H,4H)-Dioxo-2-cyclohexylisoquinoline-4-carboxylate
Methyl 1,3(2H,4H)-Dioxo-2-propargylisoquinoline-4-carboxylate
Methyl 1,3(2H,4H)-Dioxo-2-(2'-furyl)isoquinoline-4-carboxylate
i-Propyl 1,3(2H,4H)-Dioxo-2-(2'-tetrahydrofuryl)isoquinoline-4-carboxylate
i-Propyl 1,3(2H,4H)-Dioxo-2-(furfuryl)isoquinoline-4-carboxylate
i-Propyl 1,3(2H,4H)-Dioxo-2-(tetrahydrofurfuryl)isoquinoline-4-carboxylate
i-Propyl 1,3(2H,4H)-Dioxo-2-methoxyisoquinoline-4-carboxylate
i-Propyl 1,3(2H,4H)-Dioxo-2-hydroxyisoquinoline-4-carboxylate
i-Propyl 1,3(2H,4H)-Dioxo-2-benzyloxyisoquinoline-4-carboxylate
i-Propyl 1,3(2H,4H)-Dioxo-2-(o-fluorophenyl)isoquinoline-4-carboxylate
i-Propyl 1,3(2H,4H)-Dioxo-2-(p-bromophenyl)isoquinoline-4-carboxylate
n-Hexyl 1,3(2H,4H)-Dioxo-2-(p-ethoxyphenyl)isoquinoline-4-carboxylate
n-Hexyl 1,3(2H,4H)-Dioxo-2-(m-isopropylphenyl)isoquinoline-4-carboxylate
n-Hexyl 1,3(2H,4H)-Dioxo-2-(o-methylphenyl)isoquinoline-4-carboxylate
n-Hexyl 1,3(2H,4H)-Dioxo-2-(m-trifluoromethylphenyl)isoquinoline-4-carboxylate
n-Hexyl 1,3(2H,4H)-Dioxo-2-(m-nitrophenyl)isoquinoline-4-carboxylate
i-Butyl 1,3(2H,4H)-Dioxo-2-(p-aminophenyl)isoquinoline-4-carboxylate
i-Butyl 1,3(2H,4H)-Dioxo-2-(o-methylsulfonylphenyl)isoquinoline-4-carboxylate
i-Butyl 1,3(2H,4H)-Dioxo-2-(m-trifluoromethylsulfonylphenyl)isoquinoline-4-carboxylate
i-Butyl 1,3(2H,4H)-Dioxo-2-(m-dimethylsulfonamidophenyl)isoquinoline-4-carboxylate i-Butyl 1,3(2H,4H)-Dioxo-2-(p-acetamidophenyl-)isoquinoline-4-carboxylate
Ethyl 1,3(2H,4H)-Dioxo-2-(o-hydroxyphenyl-)isoquinoline-4-carboxylate
Ethyl 1,3(2H,4H)-Dioxo-2-(o-fluorobenzyl-)isoquinoline-4-carboxylate
Ethyl 1,3(2H,4H)-Dioxo-2-(p-bromobenzyl-)isoquinoline-4-carboxylate
Ethyl 1,3(2H,4H)-Dioxo-2-(p-ethoxybenzyl-)isoquinoline-4-carboxylate
Ethyl 1,3(2H,4H)-Dioxo-2-(m-isopropylbenzyl-)isoquinoline-4-carboxylate
Ethyl 1,3(2H,4H)-Dioxo-2-(o-methylbenzyl-)isoquinoline-4-carboxylate
Ethyl 1,3(2H,4H)-Dioxo-2-(m-trifluoromethylbenzyl)isoquinoline-4-carboxylate
Ethyl 1,3(2H,4H)-Dioxo-2-(m-nitrobenzyl)isoquinoline-4-carboxylate
Ethyl 1,3(2H,4H)-Dioxo-2-(p-aminobenzyl-)isoquinoline-4-carboxylate
Ethyl 1,3(2H,4H)-Dioxo-2-(o-methylsulfonylbenzyl-)isoquinoline-4-carboxylate
Ethyl 1,3(2H,4H)-Dioxo-2-(m-trifluoromethylsulfonylbenzyl)isoquinoline-4-carboxylate
Ethyl 1,3(2H,4H)-Dioxo-2-(m-dimethylsulfonamidobenzyl)isoquinoline-4-carboxylate
Ethyl 1,3(2H,4H)-Dioxo-2-(p-acetamidobenzyl-)isoquinoline-4-carboxylate
Ethyl 1,3(2H,4H)-Dioxo-2-(o-hydroxybenzyl-)isoquinoline-4-carboxylate

EXAMPLE XXII 1,3(2H,4H)-Dioxo-2-methylisoquinoline-4-(N,N-tetramethylene)carboxamide A solution of ethyl 1,3(2H,4H)-dioxo-2-methylisoquinoline-4-carboxylate (6.2 g., 0.025 mole) and pyrrolidine (1.8 g., 0.026 mole) in 100 ml. of xylene was refluxed for 4 hours, during which time solvent was distilled off until the temperature of solvent vapors in the distilling head was within two degrees of the temperature of the reaction mixture. The volume of the reaction mixture was maintained by occasional addition of xylene. The mixture was then allowed to cool, and the resulting crystals were collected by filtration, dried and recrystallized from acetonitrile to give 1,3(2H,4H)-dioxo-2-methylisoquinoline-4-(N,N-tetramethylene)carboxamide, m.p. 182°–184° C.

Anal. Calc'd. for $C_{15}H_{16}N_2O_3$: C, 66.16; H, 5.92; N, 10.29. Found: C, 66.28; H, 5.86; N, 10.37.

EXAMPLE XXIII

The procedure of Example XXII was repeated, using equivalent amounts of appropriate amines in place of said pyrrolidine, to produce the following compounds:

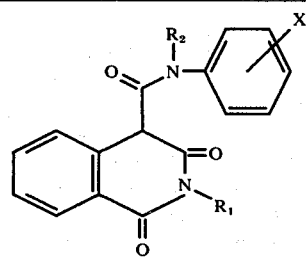

| $R_1$ | $R_2$ | X | M.p. °C. | Anal: Calc'd C | H | N | Found C | H | N |
|---|---|---|---|---|---|---|---|---|---|
| H | H | 2',5'-diCl | 242–243 (dec.) | 55.03 | 2.89 | 8.02 | 54.77 | 2.90 | 8.01 |
| H | H | 3',4'-diCH₃ | 245–248 (dec.) | 70.11 | 5.23 | 9.09 | 70.00 | 5.22 | 8.79 |
| H | H | 3',4'-diCl | 239–241 (dec.) | 55.03 | 2.89 | 8.02 | 55.28 | 2.93 | 8.29 |
| H | H | 2',5'-diOCH₃ | 197–198 (dec.) | 63.52 | 4.74 | 8.23 | 63.26 | 4.65 | 8.15 |
| CH₃ | CH₃ | H | 160–162 | 70.11 | 5.23 | 9.09 | 69.86 | 5.22 | 9.06 |
| CH₃ | CH₃ | 4'-Cl | 156–158 | 63.07 | 4.41 | 8.17 | 62.76 | 4.46 | 8.18 |
| CH₃ | H | 4'-Br | 227–228 (dec.) | 54.71 | 3.51 | 7.51 | 54.96 | 3.45 | 7.45 |
| CH₃ | H | 4'-F | 221–222 (dec.) | 65.38 | 4.19 | 8.97 | 65.02 | 4.17 | 9.01 |
| CH₃ | H | 4'-CF₃ | 210–211 (dec.) | 59.67 | 3.62 | 7.73 | 59.99 | 3.65 | 7.87 |
| CH₃ | H | 2',3'-diCl | 217–219 (dec.) | 56.21 | 3.33 | 7.71 | 56.44 | 3.36 | 7.92 |
| CH₃ | H | 2',4'-diCl | 204–205 (dec.) | 56.21 | 3.33 | 7.71 | 56.54 | 3.38 | 7.95 |
| CH₃ | H | 2'-COOC₂H₅ | 128–130 | 65.56 | 4.95 | 7.65 | 65.42 | 5.04 | 7.63 |
| CH₃ | H | 4'-COOC₂H₅ | 229–230 (dec.) | 65.56 | 4.95 | 7.65 | 65.57 | 4.89 | 7.70 |
| CH₃ | H | 5'-Cl—2'-OCH₃ | 208.5–209.5 (dec.) | 60.25 | 4.21 | 7.81 | 60.37 | 4.81 | 7.94 |
| CH₃ | H | 3',5'-diCl | 228–229.5 (dec.) | 56.21 | 3.33 | 7.71 | 55.97 | 3.16 | 7.75 |
| CH₃ | H | 3',5'-diOCH₃ | 209–210 (dec.) | 64.40 | 5.12 | 7.91 | 64.41 | 5.19 | 8.34 |
| CH₃ | H | 2',6'diCH₃ | 250 (dec.) | 70.79 | 5.63 | 8.69 | 70.91 | 5.79 | 8.91 |
| CH₃ | H | 2'-OCH₃-5'-CH₃ | 212.5–214 (dec.) | 67.44 | 5.36 | 8.28 | 67.44 | 5.50 | 8.40 |
| CH₃ | H | 2',4'-diCH₃ | 227–228 (dec.) | 70.79 | 5.63 | 8.69 | 70.84 | 5.52 | 8.68 |
| CH₃ | H | 2',5'-diCH₃ | 243.5–244 (dec.) | 70.79 | 5.63 | 8.69 | 70.82 | 5.36 | 8.71 |
| CH₃ | H | 3'-Cl—4'-CH₃ | 213–214 (dec.) | 63.07 | 4.41 | 8.17 | 63.31 | 4.38 | 8.15 |
| CH₃ | H | 3'-CO—CH₃ | 177–178 (dec.) | 67.85 | 4.80 | 8.33 | 67.55 | 4.83 | 8.52 |
| CH₃ | H | 3'-Cl—2'-CH₃ | 240–240.5 (dec.) | 63.07 | 4.41 | 8.17 | 63.14 | 4.34 | 8.17 |
| CH₃ | H | 3',5'-diCH₃ | 253–254 (dec.) | 70.79 | 5.63 | 8.69 | 70.52 | 5.78 | 8.77 |
| CH₃ | H | 2'-Cl—4'-CH₃ | 202.5–204 (dec.) | 63.07 | 4.41 | 8.17 | 63.23 | 4.38 | 8.15 |
| CH₃ | H | 2'-CH₃—4'-OCH₃ | 213.5–214 (dec.) | 67.44 | 5.36 | 8.28 | 67.14 | 5.41 | 8.17 |
| CH₃ | H | 4'-Cl—2'-CH₃ | 237–238 (dec.) | 63.07 | 4.41 | 8.17 | 62.88 | 4.37 | 8.29 |
| CH₃ | H | 2'-Cl—5'-CF₃ | 205–206 (dec.) | 54.49 | 3.05 | 7.06 | 54.65 | 3.12 | 7.11 |
| H | H | 2',4'-diOCH₃ | 223–225 (dec.) | 63.52 | 4.74 | 8.23 | 63.75 | 4.69 | 8.51 |
| H | H | 4'-F | 242–244 (dec.) | 64.42 | 3.72 | 9.39 | 64.55 | 3.78 | 9.61 |
| H | H | 4'-CF₃ | 250–251 (dec.) | 58.62 | 3.18 | 8.05 | 58.89 | 3.25 | 8.41 |
| H | H | 4'-Br | 246–248 (dec.) | 53.50 | 3.09 | 7.80 | 53.79 | 3.04 | 7.90 |

EXAMPLE XXIV

The procedure of Example XXII is repeated, using equivalent amounts of appropriate amines in place of said pyrrolidine, to produce the following compounds:

| R₁ | R₂ | R₃ |
|---|---|---|
| hexyl | ethoxyethyl | ethyl |
| benzyloxy | hydrogen | 1,1-dimethyl-2-butynyl |
| methoxy | methoxyethyl | 3-acetylphenyl |
| hexyl | hydrogen | t-butyl |
| cyclopropyl | methyl | n-hexyl |
| cyclohexyl | i-propyl | 3-hexenyl |
| 2-furyl | n-hexyl | propargyl |
| 2-tetrahydrofuryl | allyl | cyclopropyl |
| furfuryl | 2,3-dimethyl-3-butenyl | trifluoromethyl |
| tetrahydrofurfuryl | hydrogen | hexafluoroisopropyl |
| ethyl | hydrogen | adamantyl |
| p-bromophenyl | hydrogen | butynyl |
| p-ethoxyphenyl | ethyl | tetrahydrofurfuryl |
| m-isopropylphenyl | n-propyl | pyridyl |
| o-methylphenyl | neopentyl | 3-fluoro-5-propylphenyl |
| m-trifluoromethylphenyl | hydrogen | 2,5-dinitrophenyl |
| m-nitrophenyl | methyl | 4-aminophenyl |
| p-aminophenyl | i-propyl | 3,5-bis-methylsulfonylphenyl |
| o-methylsulfonylphenyl | hydrogen | 4-trifluoromethylsulfonylphenyl |
| m-trifluoromethyl-sulfonylphenyl | n-hexyl | 2-methyl-4-dimethylsulfonamido-phenyl |
| m-dimethylsulfonamido-phenyl | allyl | 3-bromo-5-acetamidophenyl |
| p-acetamidophenyl | 2,3-dimethyl-3-butenyl | 2,5-dihydroxyphenyl |
| o-hydroxyphenyl | hydrogen | 2-fluoronaphthyl |
| o-fluorobenzyl | methyl | 3-chloronaphthyl |
| p-bromobenzyl | hydrogen | 4-bromonaphthyl |
| p-ethoxybenzyl | ethyl | 5-ethoxynaphthyl |
| m-isopropylbenzyl | n-propyl | 5-isopropylnaphthyl |
| o-methylbenzyl | neopentyl | 5-trifluoromethylnaphthyl |
| m-nitrobenzyl | methyl | 2-aminonaphthyl |
| p-aminobenzyl | i-propyl | 5-methylsulfonylnaphthyl |
| o-methylsulfonylbenzyl | hydrogen | 5-trifluoromethylsulfonyl-naphthyl |
| m-trifluoromethyl-sulfonylbenzyl | n-hexyl | 5-dimethylsulfonamidonaphthyl |
| m-dimethylsulfonamido-benzyl | allyl | 3-acetamidonaphthyl |
| p-acetamidobenzyl | 2,3-dimethyl-3-butenyl | 4-hydroxynaphthyl |
| o-hydroxybenzyl | hydrogen | 2'-fluorobenzyl |
| hexyl | hydrogen | 3'-chlorobenzyl |
| cyclopropyl | hydrogen | 4'-bromobenzyl |
| cyclohexyl | ethyl | 4'-ethoxybenzyl |
| propargyl | n-propyl | 3'-i-propylbenzyl |
| 2-furyl | neopentyl | 2'-trifluoromethylbenzyl |
| 2-tetrahydrofuryl | hydrogen | 4'-nitrobenzyl |
| furfuryl | methyl | 2'-aminobenzyl |
| tetrahydrofurfuryl | i-propyl | 4'-methylsulfonylbenzyl |
| o-fluorophenyl | hydrogen | 4'-trifluoromethylsulfonylbenzyl |
| p-bromophenyl | n-hexyl | 3'-dimethylsulfonamidobenzyl |
| p-ethoxyphenyl | allyl | 2'-acetamidobenzyl |
| m-isopropylphenyl | 2,3-dimethyl-3-butenyl | 2'-hydroxybenzyl |
| o-methylphenyl | hydrogen | 2'-fluoro-β-phenethyl |
| m-trifluoromethyl-phenyl | 2-CH₃-3-butynyl | 3'-Cloro-β-phenethyl |
| m-nitrophenyl | hydrogen | 4'-Bromo-β-phenethyl |
| p-aminophenyl | ethyl | 4'-ethoxy-β-phenethyl |
| o-methylsulfonylphenyl | n-propyl | 3'-i-propyl-β-phenethyl |
| m-trifluoromethyl-sulfonylphenyl | neopentyl | 2'-trifluoromethyl-β-phenethyl |
| m-dimethylsulfonamido-phenyl | H | 4'-nitro-β-phenethyl |
| p-acetamidophenyl | methyl | 2'-amino-β-phenethyl |
| o-hydroxyphenyl | i-propyl | 4'-methylsulfonyl-β-phenethyl |
| o-fluorobenzyl | hydrogen | 4'-trifluoromethyl-β-phenethyl |
| p-bromobenzyl | n-hexyl | 3'-dimethylsulfonamido-β-phenethyl |
| p-ethoxybenzyl | allyl | 2'-acetamido-β-phenethyl |
| m-isopropylbenzyl | 2,3-diCH₃-3-butenyl | 2'-hydroxy-β-phenethyl |
| o-methylbenzyl | hexamethyleneimine | |
| m-trifluoromethylbenzyl | piperazine | |
| m-nitrobenzyl | N-methylpiperazine | |
| p-aminobenzyl | N-phenylpiperazine | |

EXAMPLE XXV

Each of the following 1,3(2H,4H)-dioxoisoquinoline-4-carboxamides were tested for anti-inflammatory activity using the carrageenin rat food edema test and were found to be active at the indicated dosage level:

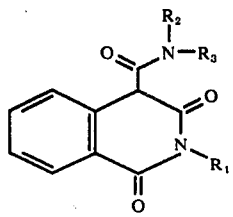

| R₁ | R₂ | R₃ | Dosage, mg/kg |
|---|---|---|---|
| CH₃ | H | phenyl | 3.3 |
| CH₃ | H | 2-chlorophenyl | 33 |
| CH₃ | H | 3-chlorophenyl | 100 |
| CH₃ | H | 4-chlorophenyl | 3.3 |
| CH₃ | H | 2-methylphenyl | 3.3 |
| CH₃ | H | 3-methylphenyl | 100 |
| CH₃ | H | 4-methylphenyl | 33 |
| CH₃ | H | 2-methoxyphenyl | 3.3 |
| CH₃ | H | 4-methoxyphenyl | 3.3 |
| CH₃ | H | 2,5-dichlorophenyl | 3.3 |
| CH₃ | H | 3,4-dimethylphenyl | 33 |
| CH₃ | H | 3,4-dichlorophenyl | 10 |
| CH₃ | H | 3-trifluoromethylphenyl | 10 |
| CH₃ | H | 2,4-dimethoxyphenyl | 33 |
| CH₃ | H | 2,5-dimethoxyphenyl | 33 |
| CH₃ | H | 2-ethoxyphenyl | 200 |
| CH₃ | H | 4-ethoxyphenyl | 200 |
| H | H | phenyl | 33 |
| H | H | 2-chlorophenyl | 100 |
| H | H | 3-chlorophenyl | 33 |
| H | H | 4-chlorophenyl | 3.3 |
| H | H | 3-methylphenyl | 33 |
| H | H | 4-methylphenyl | 100 |
| H | H | 2-methoxyphenyl | 100 |
| H | H | 4-methoxyphenyl | 100 |
| CH₃ | H | H | 33 |
| CH₃ | H | ethyl | 33 |
| CH₃ | H | n-propyl | 100 |
| CH₃ | H | n-butyl | 200 |
| CH₃ | H | cyclohexyl | 200 |
| CH₃ | —(CH₂)₅— | | 100 |
| CH₃ | —(CH₂)₂—O—(CH₂)₂— | | 100 |
| CH₃ | —(CH₂)₄— | | 100 |
| CH₃ | H | allyl | 10 |
| CH₃ | H | o-methoxybenzyl | 100 |
| CH₃ | H | 3',4'-dichlorobenzyl | 200 |
| CH₃ | H | benzyl | 10 |
| CH | H | β-phenethyl | 100 |
| CH | H | carbethoxymethyl | 200 |
| CH | CH₃ | phenyl | 33 |
| H | H | ethyl | 200 |
| H | H | cyclohexyl | 200 |
| m-chlorophenyl | H | ethyl | 200 |
| m-chlorophenyl | H | n-propyl | 200 |
| m-chlorophenyl | H | cyclohexyl | 200 |
| m-chlorophenyl | H | benzoyl | 200 |
| m-chlorophenyl | H | carbethoxymethyl | 200 |
| m-chlorophenyl | H | 2,5-dichlorophenyl | 3.3 |
| m-chlorophenyl | H | phenyl | 200 |
| β-phenethyl | H | phenyl | 200 |
| β-phenethyl | H | ethyl | 200 |
| β-phenethyl | H | 4-chlorophenyl | 200 |
| i-propyl | H | ethyl | 200 |
| benzyl | H | phenyl | 200 |
| allyl | H | ethyl | 100 |
| allyl | H | phenyl | 200 |
| 3-pyridyl | H | phenyl | 200 |
| 3-pyridyl | H | 4-chlorophenyl | 200 |
| phenyl | H | H | 200 |
| CH₃ | H | 4-bromophenyl | 33 |
| CH₃ | H | 4-fluorophenyl | 3.3 |
| CH₃ | H | 4-trifluoromethylphenyl | 33 |
| CH₃ | H | 2,3-dichlorophenyl | 33 |
| CH₃ | H | 2,4-dichlorophenyl | 3.3 |
| CH₃ | H | 2-carbethoxyphenyl | 100 |
| CH₃ | H | 4-carbethoxyphenyl | 100 |
| CH₃ | H | 5-chloro-2-methoxyphenyl | 33 |
| CH₃ | H | 3,5-dichlorophenyl | 33 |
| CH₃ | H | 3,5-dimethoxyphenyl | 100 |
| CH₃ | H | 2,6-dimethylphenyl | 200 |
| CH₃ | H | 2-methoxy-5-methylphenyl | 200 |
| CH₃ | H | 2,4-dimethylphenyl | 100 |
| CH₃ | H | 2,5-dimethylphenyl | 100 |
| CH₃ | H | 3-chloro-4-methylphenyl | 100 |
| CH₃ | H | 3-acetylphenyl | 100 |
| CH₃ | H | 3-chloro-2-methylphenyl | 200 |
| CH₃ | H | 3,5-dimethylphenyl | 200 |
| CH₃ | H | 2-chloro-4-methylphenyl | 100 |
| CH₃ | H | 2-chloro-4-methoxyphenyl | 100 |
| CH₃ | H | 4-chloro-2-methylphenyl | 100 |
| CH₃ | H | 2-chloro-5-trifluoromethyl | 200 |

EXAMPLE XXVI 2-(m-Chlorophenyl)-7-Chloroisoquinoline-1,3(2H,4H)-dione

A mixture of 4-chlorohomophthalic acid (54.0 g., 0.25 mole) and m-chloroaniline (31.8 g., 0.25 mole) is heated by an oil bath until molten for two hours. When removed from the oil bath, the reaction mixture solidifies and is recrystallized twice from ethanol/ethyl acetate, giving 2-(m-Chlorophenyl)-7-chloroisoquinoline-1,3(2H,4H)-dione.

EXAMPLE XXVII

2-Allyl-5-methoxyisoquinoline-1,3(2H,4H)-dione

A mixture of 6-methoxyhomophthalic acid (9.7 g., 0.05 mole) and allylamine (2.8 g., 0.05 mole) is heated by an oil bath until molten for 40 minutes. The mixture solidifies upon cooling and is recrystallized from isopropanol, giving 2-allyl-5-methoxyisoquinoline-1,3(2H,4H)-dione.

EXAMPLE XXVIII

2-Isopropyl-6,7-dimethylisoquinoline-1,3(2H,4H)-dione

A mixture of 4,5-dimethylhomophthalic acid (104 g., 0.5 mole) and isopropylamine (59 g., 1 mole) is heated by an oil bath until molten for 90 minutes. The hot mixture is then poured into 600 ml. of ethanol, treated with carbon black and filtered. The mixture is concentrated to about 300 ml. and slowly cooled to room temperature. 2-Isopropyl-6,7-dimethylisoquinoline-1,3(2H,4H)-dione precipitates and is collected by filtration.

EXAMPLE XXIX

The following products are prepared by the procedure of Example XXVI by substituting an appropriate amine in place of said m-chloroaniline and an appropriately substituted homophthalic acid in place of said 4-chlorohomophthalic acid:

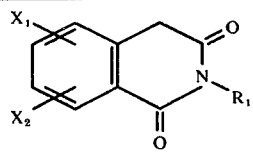

| R₁ | X₁ | X₂ |
| --- | --- | --- |
| hexyl | hydrogen | 7-chloro |
| cyclopropyl | 6-methoxy | 7-methoxy |
| cyclohexyl | hydrogen | 7-methoxy |
| propargyl | 6-methoxy | hydrogen |
| 2'-furyl | 5-nitro | hydrogen |
| 2'-tetrahydrofuryl | 6-fluoro | 8-propyl |
| furfuryl | 5-nitro | 8-nitro |
| tetrahydrofurfuryl | hydrogen | 7-amino |
| methoxy | 6-chloro | 7-chloro |
| hydroxy | 6-methyl | 7-methyl |
| benzyloxy | hydrogen | 7-chloro |
| phenyl | 6-chloro | 7-chloro |
| o-fluorophenyl | 6-methylsulfonyl | 7-methylsulfonyl |
| p-bromophenyl | hydrogen | 7-trifluoromethylsulfonyl |
| p-ethoxyphenyl | 5-methyl | 7-dimethylsulfonamido |
| m-isopropylphenyl | 6-bromo | 8-acetamido |
| o-methylphenyl | 5-hydroxy | 8-hydroxy |
| m-trifluoromethylphenyl | 6-fluoro | hydrogen |
| m-nitrophenyl | hydrogen | 8-chloro |
| p-aminophenyl | 5-bromo | hydrogen |
| o-methylsulfonylphenyl | 6-ethoxy | hydrogen |
| m-trifluoromethylsulfonylphenyl | hydrogen | 7-isopropyl |
| m-dimethylsulfonamidophenyl | hydrogen | 7-amino |
| p-acetamidophenyl | hydrogen | 7-trifluoromethyl |
| o-hydroxyphenyl | 6-methylsulfonyl | 7-chloro |
| benzyl | hydrogen | 7-ethoxy |
| o-fluorobenzyl | hydrogen | 7-fluoro |
| p-bromobenzyl | hydrogen | 7-chloro |
| p-ethoxybenzyl | hydrogen | 8-bromo |
| m-isopropylbenzyl | hydrogen | 7-ethoxy |
| o-methylbenzyl | hydrogen | 6-isopropyl |
| m-trifluoromethylbenzyl | hydrogen | 6-trifluoromethyl |
| m-nitrobenzyl | hydrogen | 5-nitro |
| p-aminobenzyl | hydrogen | 6-amino |
| o-methylsulfonylbenzyl | hydrogen | 7-methylsulfonyl |
| m-trifluoromethylsulfonylbenzyl | hydrogen | 7-trifluoromethylsulfonyl |
| m-dimethylsulfonamidobenzyl | hydrogen | 7-dimethylsulfonamido |
| p-acetamidobenzyl | hydrogen | 6-acetamido |
| p-acetamidobenzyl | hydrogen | 7-hydroxy |
| o-hydroxybenzyl | hydrogen | 7-chloro |

EXAMPLE XXX

7-Chloro-2-methyl-1,3(2H,4H)-dioxoisoquinoline-4-carboxamide

A solution of potassium cyanate (2.84 g., 0.035 mole) in 10 ml. of water is added with stirring, over a 30 minute period, to a solution of 7-chloro-2-methyl-1,3(2H,4H)-dioxoisoquinoline (5.3 g., 0.025 mole) in 20 ml. of dimethyl-formamide which has been heated over a steam bath. The resulting solution is heated for an additional two hours and then poured into an excess of ice water containing 10 ml. of 6N hydrochloric acid. The resulting precipitate is filtered, dried and recrystallized from acetonitrile to give the desired 7-chloro-2-methyl-1,3(2H,4H)-dioxoisoquinoline-4-carboxamide.

EXAMPLE XXXI

The procedure of Example XXX is repeated, using equivalent amounts of the products of Examples XXVI - XXIX in place of said 7-chloro-2-methyl-1,3(2H,4H)-dioxoisoquinoline, to prepare the following products:

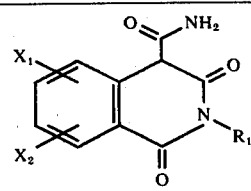

| R₁ | X₁ | X₂ |
| --- | --- | --- |
| m-chlorophenyl | hydrogen | 7-chloro |
| allyl | 5-methoxy | hydrogen |
| isopropyl | 6-methoxy | 7-methoxy |
| hexyl | hydrogen | 7-chloro |
| cyclopropyl | 6-methoxy | 7-methoxy |
| cyclohexyl | hydrogen | 7-methoxy |
| propargyl | 6-methoxy | hydrogen |
| 2'-furyl | 5-nitro | hydrogen |
| 2'-tetrahydrofuryl | 6-fluoro | 8-propyl |
| furfuryl | 5-nitro | 8-nitro |
| tetrahydrofurfuryl | hydrogen | 7-amino |

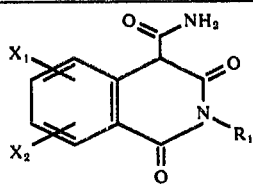

| R₁ | X₁ | X₂ |
|---|---|---|
| methoxy | 6-chloro | 7-chloro |
| hydroxy | 6-methyl | 7-methyl |
| benzyloxy | hydrogen | 7-chloro |
| phenyl | 6-chloro | 7-chloro |
| o-fluorophenyl | 6-methylsulfonyl | 7-methylsulfonyl |
| p-bromophenyl | hydrogen | 7-trifluoromethylsulfonyl |
| p-ethoxyphenyl | 5-methyl | 7-dimethylsulfonamido |
| m-isopropylphenyl | 6-bromo | 8-acetamido |
| o-methylphenyl | 5-hydroxy | 8-hydroxy |
| m-trifluoromethylphenyl | o-fluoro | hydrogen |
| m-nitrophenyl | hydrogen | 8-chloro |
| p-aminophenyl | 5-bromo | hydrogen |
| o-methylsulfonylphenyl | 6-ethoxy | hydrogen |
| m-trifluoromethylsulfonylphenyl | hydrogen | 7-isopropyl |
| m-dimethylsulfonamidophenyl | hydrogen | 7-amino |
| p-acetamidophenyl | hydrogen | 7-trifluoromethyl |
| o-hydroxyphenyl | 6-methylsulfonyl | 7-chloro |
| benzyl | hydrogen | 7-ethoxy |
| o-fluorobenzyl | hydrogen | 7-fluoro |
| p-bromobenzyl | hydrogen | 7-chloro |
| p-ethoxybenzyl | hydrogen | 8-bromo |
| m-isopropylbenzyl | hydrogen | 7-ethoxy |
| o-methylbenzyl | hydrogen | 6-isopropyl |
| m-trifluoromethylbenzyl | hydrogen | 6-trifluoromethyl |
| m-nitrobenzyl | hydrogen | 5-nitro |
| p-aminobenzyl | hydrogen | 6-amino |
| o-methylsulfonylbenzyl | hydrogen | 7-methylsulfonyl |
| m-trifluoromethylsulfonylbenzyl | hydrogen | 7-trifluoromethylsulfonyl |
| m-dimethylsulfonamidobenzyl | hydrogen | n-dimethylsulfonamido |
| p-acetamidobenzyl | hydrogen | 6-acetamido |
| p-acetamidobenzyl | hydrogen | 7-hydroxy |
| o-hydrobenzyl | hydrogen | 7-chloro |

EXAMPLE XXXII

7-Chloro-2-methyl-1,3(2H,4H)-dioxoisoquinoline-4-carboxanilide

A solution containing 7-chloro-2-methyl-1,3(2H,4H)-dioxoisoquinoline (5.2 g., 0.025 mole), triethylamine (2.6 g., 0.026 mole) and phenylisocyanate (3.1 g., 0.026 mole) in 100 ml. of tetrahydrofuran was refluxed for 2 hours. The solution was then poured into an excess of ice water containing 5 ml. of hydrochloric acid. The resulting precipitate was collected by filtration. washed with water, dried and recrystallized from acetic acid, to give 7-chloro-2-methyl-1,3(2H,4H)-dioxoisoquinoline-4-carboxanilide, m.p. 238°–239° C. (dec.).

Anal. Calc'd. for $C_{17}H_{13}N_2O_3Cl$: C, 62.10; H, 3.98; N. 8.52. Found: C, 62.10; H, 3.89; N, 8.52.

EXAMPLE XXXIII

The procedure of Example XXXII was repeated, using equivalent amounts of appropriately substituted substrates, to produce the following compounds:

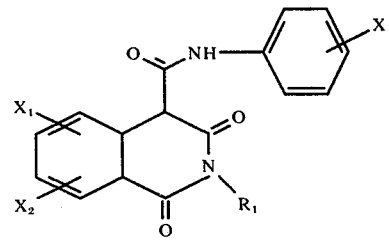

| R₁ | X | X₁ | X₂ | M.p., ° C. | Anal.: Calc'd. C | H | N | Found C | H | N |
|---|---|---|---|---|---|---|---|---|---|---|
| CH₃ | 4'-Cl | 6-OCH₃ | 7-OCH₃ | 227–228 (dec.) | 58.69 | 4.41 | 7.21 | 58.48 | 4.34 | 7.26 |
| CH₃ | H | 6-OCH₃ | 7-OCH₃ | 237–238 (dec.) | 64.40 | 5.12 | 7.91 | 64.52 | 5.18 | 8.14 |
| CH₃ | 4'-OCH₃ | H | 7-OCH₃ | 222–224 | 64.40 | 5.12 | 7.91 | 64.63 | 5.23 | 8.00 |
| CH₃ | 4'-Cl | H | 7-OCH₃ | 222 | 60.25 | 4.21 | 7.81 | 59.90 | 4.31 | 7.86 |
| CH₃ | H | H | 7-OCH₃ | 223–225 (dec.) | 66.65 | 4.97 | 8.64 | 66.86 | 4.91 | 8.82 |
| CH₃ | 2'-OCH₃ | H | 7-OCH₃ | 192–194 | 64.40 | 5.12 | 7.91 | 64.44 | 5.09 | 7.93 |
| CH₃ | 2'-Cl | H | 7-OCH₃ | 216.5–217 (dec.) | 60.25 | 4.21 | 7.81 | 60.48 | 4.24 | 8.04 |
| CH₃ | 2'-Cl | 6-OCH₃ | 7-OCH₃ | 247–249 (dec.) | 58.70 | 4.41 | 7.21 | 58.60 | 4.41 | 7.35 |
| H | H | 6-OCH₃ | 7-OCH₃ | 251–252 (dec.) | 63.52 | 4.74 | 8.23 | 63.56 | 4.82 | 8.19 |
| H | H | H | 7-Cl | 224–226 (dec.) | 61.06 | 3.52 | 8.90 | 61.06 | 3.47 | 8.85 |
| H | H | H | 7-OCH₃ | 271–273 (dec.) | 65.80 | 4.55 | 9.03 | 65.52 | 4.57 | 9.16 |

EXAMPLE XXXIV

The procedure of Example XXXIII is repeated, using equivalent amounts of appropriately substituted substrates to produce the following compounds:

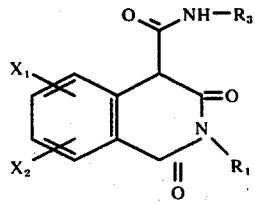

| $R_1$ | $R_3$ | $X_1$ | $X_2$ |
|---|---|---|---|
| neopentyl | acetyl | hydrogen | 7-chloro |
| hydrogen | butyryl | 6-methoxy | 7-methoxy |
| phenyl | benzoyl | 5-nitro | hydrogen |
| m-trifluoromethylbenzyl | 3-nitrophenyl | 6-amino | hydrogen |
| methyl | n-butyl | 5-methyl | 8-methyl |
| m-chlorophenyl | benzoyl | 5-methyl | hydrogen |
| methyl | carbethoxymethyl | hydrogen | 7-hydroxy |

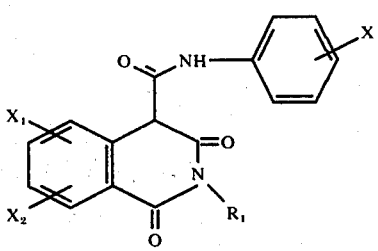

| $R_1$ | X | $X_1$ | $X_2$ |
|---|---|---|---|
| methyl | hydrogen | 6-fluoro | 8-propyl |
| methyl | 2-chloro | 5-nitro | 8-nitro |
| methyl | 3-chloro | hydrogen | 7-amino |
| methyl | 4-chloro | 6-chloro | 7-chloro |
| methyl | 3-methyl | 6-methylsulfonyl | 7-methylsulfonyl |
| methyl | 4-methyl | hydrogen | 7-trifluoromethyl |
| methyl | 2-methoxy | 6-bromo | 8-acetamido |
| methyl | 4-methoxy | 5-hydroxy | 8-hydroxy |
| methyl | 2-ethoxy | hydrogen | 7-isopropyl |
| methyl | 4-ethoxy | 6-ethoxy | 7-ethoxy |
| m-chlorophenyl | hydrogen | 6-methylsulfonyl | 7-chloro |
| benzyl | hydrogen | hydrogen | 8-bromo |
| allyl | hydrogen | 5-nitro | hydrogen |

EXAMPLE XXXV 6,7-Dimethoxy-1,3(2H,4H)-dioxoisoquinoline-4-(N-ethyl)carboxamide To a stirred mixture of 6,7-dimethoxy-1,3(2H,4H)-dioxoisoquinoline (5.5 g., 0.025 mole) and triethylamine (2.6 g., 0.026 mole) in 10 ml. of dimethysulfoxide was added dropwise, over a five minute period, a solution of ethylisocyanate (1.86 g., 0.026 mole) in 10 ml. of dimethylsulfoxide. After stirring for 2 hours, the solution was poured into an excess of ice water containing 5 ml. of hydrochloric acid. The resulting precipitate was collected by filtration, washed with water, dried and recrystallized from acetonitrile to give 6,7-dimethoxy-1,3(2H,4H)-dioxoisoquinoline-4-(N-ethyl)carboxamide, m.p. 255°–257° C. (dec.).

Anal. Calc'd. for $C_{14}H_{16}N_2O_5$: C, 57.53; H, 5.52; N, 9.59. Found: C, 57.55; H, 5.65; N, 9.34.

EXAMPLE XXXVI

The procedure of Example XXXXV was repeated, using equivalent amounts of appropriate substrates in place of said 6,7-dimethoxy-1,3(2H,4H)-dioxoisoquinoline and ethylisocyanate, to produce the following compounds:

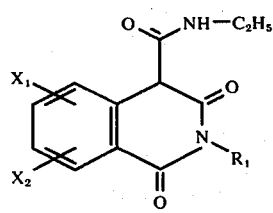

| $R_1$ | $X_1$ | $X_2$ | M.p.° C. | Anal: Calc'd C | H | N | Found C | H | N |
|---|---|---|---|---|---|---|---|---|---|
| $CH_3$ | H | 7-Cl | 218–219 (dec.) | 55.62 | 4.67 | 9.98 | 55.69 | 4.71 | 9.93 |
| $CH_3$ | 6-$OCH_3$ | 7-$OCH_3$ | 250–251 (dec.) | 58.81 | 5.92 | 9.15 | 59.12 | 5.93 | 9.01 |
| H | H | 7-Cl | 237–238 (dec.) | 54.04 | 4.16 | 10.51 | 54.01 | 4.37 | 10.59 |

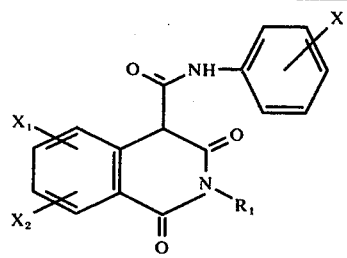

| $R_1$ | X | $X_1$ | $X_2$ | M.p.° C. | Anal: Calc'd | | | Found | | |
|---|---|---|---|---|---|---|---|---|---|---|
| | | | | | C | H | N | C | H | N |
| $CH_3$ | 2,5-diCl | H | 7-$OCH_3$ | 210–211 | 54.98 | 3.59 | 7.15 | 55.08 | 3.76 | 7.17 |
| $CH_3$ | 2-$CH_3$ | 6-$OCH_3$ | 7-$OCH_3$ | 242–243 (dec.) | 65.20 | 5.47 | 7.61 | 65.33 | 5.39 | 7.71 |
| H | 4-Cl | 6-$OCH_3$ | 7-$OCH_3$ | 260–261 (dec.) | 57.68 | 4.03 | 7.48 | 57.76 | 4.09 | 7.53 |
| H | 4-Cl | H | 7-Cl | 240–241 (dec.) | 55.03 | 2.89 | 8.02 | 55.12 | 2.83 | 8.26 |
| H | H | H | 7-$OCH_3$ | 271–273 (dec.) | 65.80 | 4.55 | 9.03 | 65.52 | 4.57 | 9.16 |
| H | 4-Cl | H | 7-$OCH_3$ | 280–282 (dec.) | 59.22 | 3.80 | 8.13 | 59.15 | 3.71 | 8.06 |

EXAMPLE XXXVII

The procedure of Example XXXV is repeated, using equivalent amounts of appropriate substrates in place of said 6,7-dimethoxy-1,3(2H,4H)-dioxoisoquinoline and ethylisocyanate, to produce the following compounds:

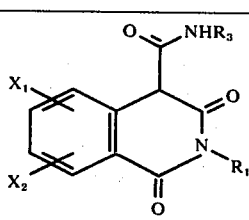

| $R_1$ | $R_3$ | $X_1$ | $X_2$ |
|---|---|---|---|
| H | $C_2H_5$ | 5-$NO_2$ | H |
| H | $C_6H_{11}$ | 6-F | 8-F |
| $CH_3$ | $C_2H_5$ | 5-$NO_2$ | 8-$NO_2$ |
| $CH_3$ | $CH_3CH_2CH_2$ | H | 7-$NH_2$ |
| $CH_3$ | $C_6H_{11}$ | 6-Cl | 7-Cl |
| $CH_3$ | $CH_3$ | 5-OH | 8-OH |
| m-Cl—$C_6H_4$— | $C_2H_5$ | 6-$CF_3$ | H |
| m-Cl—$C_6H_4$— | $CH_3CH_2CH_2$ | H | 7-$CH_3CONH$— |
| m-Cl—$C_6H_4$— | $C_6H_{11}$ | H | 7-$CH_3SO_2$— |
| m-Cl—$C_6H_4$— | $CH_2CO_2Et$ | H | 7-CH |
| $(CH_3)_2CH$— | $C_2H_5$ | 6-Br | 7-Br |
| $CH_2$:$CH$—$CH_2$— | $C_2H_5$ | 6-$OC_2H_5$ | H |

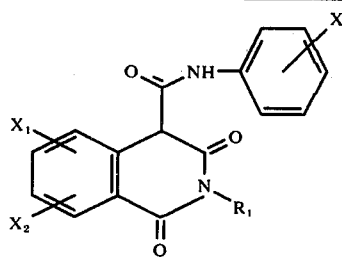

| $R_1$ | X | $X_1$ | $X_2$ |
|---|---|---|---|
| $CH_3$ | 2'-$CH_3$ | H | 7-Cl |
| $CH_3$ | 2',5'-diCl | 6-$OCH_3$ | 7-$OCH_3$ |
| H | 2'-Cl | H | 7-$OCH_3$ |
| H | 3'-Cl | 6-$OCH_3$ | H |
| H | 4'-Cl | 5-$NO_2$ | H |
| H | 2'-$CH_3$ | 6-$CH_3$ | 7-$CH_3$ |
| H | 4'-$CH_3$ | H | 7-$OC_2H_5$ |

-continued

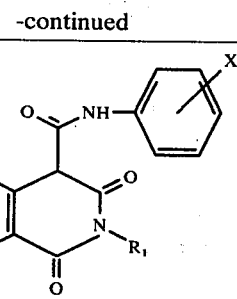

| $R_1$ | X | $X_1$ | $X_2$ |
|---|---|---|---|
| H | 2'-$OCH_3$ | 6-Br | 7-Br |
| H | 4'-$OCH_3$ | 5-$NO_2$ | 8-$NO_2$ |
| m-Cl—$C_6H_4$— | 2',5'-diCl | 6-Cl | 7-Cl |
| H | 4'-$OC_2H_5$ | H | 7-$OC_2H_5$ |
| H | 2'-$OC_2H_5$ | 6-$C_2H_5$ | 7-$C_2H_5$ |

EXAMPLE XXXVIII

7-Methoxy-2-methyl-1,3(2H,4H)-dioxoisoquinoline-4-(N-benzyl)carboxamide

A mixture of 2'-chloro-7-methoxy-2-methyl-1,3(2H,4H)-dioxoisoquinoline-4-carboxanilide (8.95 g., 0.025 mole), prepared as in Example XXXIII, and benzylamine (2.7 g., 0.025 mole) in 100 ml. of xylene is refluxed for 6 hours, after which time the mixture is allowed to cool. The resulting precipitate is collected by filtration, dried and recrystallized from xylene, giving the desired 7-methoxy-2-methyl-1,3(2H,4H)-dioxoisoquinoline-4-(N-benzyl)carboxamide.

EXAMPLE XXXIX

The procedure of Example XXXVIII is repeated, using equivalent amounts of appropriately substituted o-chlorocarboxanilides and amines, to produce the following compounds:

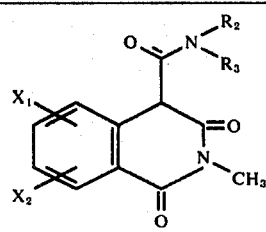

| R₂ | R₃ | X₁ | X₂ |
|---|---|---|---|
| —(CH₂)₅— | | 6-C₂H₅ | 7-C₂H₅ |
| —(CH₂)₂—O—(CH₂)₂— | | H | 7-Cl |
| H | allyl | 6-Cl | 7-Cl |
| H | 4'-OCH₃—benzyl | 5-NO₂ | H |
| H | 3',4'-diCl—benzyl | H | 7-OCH₃ |
| H | β-phenethyl | H | 7-n-C₃H₇ |

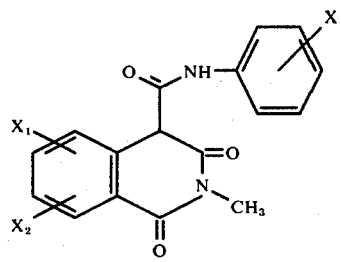

| X | X₁ | X₂ |
|---|---|---|
| 3',4'-diCH₃ | 6-n-C₃H₇ | 7-n-C₃H₇ |
| 3',4'-diCl | 5-NO₂ | 8-NO₂ |
| 3'-CF₃ | H | 7-CF₃ |
| 2',4'-diOCH₃ | 6-Cl | 7-Cl |
| 2',5'-diOCH₃ | H | 7-F |

EXAMPLE XL

Ethyl 7-Methoxy-2-methyl-1,3(2H,4H)-dioxoisoquinoline-4-carboxylate

A mixture of 2'-chloro-7-methoxy-2-methyl-1,3(2H,4H)-dioxoisoquinoline-4-carboxanilide (17.9 g., 0.05 mole), prepared as in Example XXXIII, in 125 ml. of absolute ethanol is refluxed for 4 hours. The original suspension becomes a clear solution after about 45 minutes. Following the reflux period, the solution is concentrated to one half its original volume and is then cooled slowly. The resulting precipitate is collected by filtration and dried to give the desired ethyl 7-methoxy-2-methyl-1,3(2H,4H)-dioxoisoquinoline-4-carboxylate.

EXAMPLE XLI

The procedure of Example XL is repeated, using equivalent amounts of appropriately substituted carboxanilides and appropriate alcohol in place of said o-chlorocarboxanilide and ethanol, to produce the following compounds:

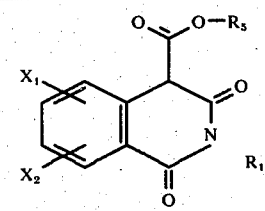

| R₁ | R₅ | X₁ | X₂ |
|---|---|---|---|
| hydrogen | ethyl | 6-chloro | 7-chloro |
| hexyl | methyl | hydrogen | 7-chloro |
| cyclopropyl | methyl | 6-methoxy | 7-methoxy |
| cyclohexyl | methyl | hydrogen | 7-methoxy |
| propargyl | methyl | 6-methoxy | hydrogen |
| 2'-furyl | methyl | 5-nitro | hydrogen |
| 2'-tetrahydrofurfuryl | i-propyl | 6-fluoro | 8-propyl |
| furfuryl | i-propyl | 5-nitro | 8-nitro |
| tetrahydrofurfuryl | i-propyl | hydrogen | 7-amino |
| methoxy | i-propyl | 6-chloro | 7-chloro |
| hydroxy | i-propyl | 6-methyl | 7-methyl |
| benzyloxy | i-propyl | hydrogen | 7-chloro |
| phenyl | i-propyl | 6-chloro | 7-chloro |
| o-fluorophenyl | i-propyl | 6-methylsulfonyl | 7-methylsulfonyl |
| p-bromophenyl | i-propyl | hydrogen | 7-trifluoromethylsulfonyl |
| p-ethoxyphenyl | n-hexyl | 5-methyl | 7-dimethylsulfonamido |
| m-isopropylphenyl | n-hexyl | 6-bromo | 8-acetamido |
| o-methylphenyl | n-hexyl | 5-hydroxy | 8-hydroxy |
| m-trifluoromethylphenyl | n-hexyl | 6-fluoro | hydrogen |
| m-nitrophenyl | n-hexyl | hydrogen | 8-chloro |
| p-aminophenyl | i-butyl | 5-bromo | hydrogen |
| o-methylsulfonylphenyl | i-butyl | 6-ethoxy | hydrogen |
| m-trifluoromethylsulfonylphenyl | i-butyl | hydrogen | 7-isopropyl |
| m-dimethylsulfonamidophenyl | i-butyl | hydrogen | 7-amino |
| p-acetamidophenyl | i-butyl | hydrogen | 7-trifluoromethyl |

-continued

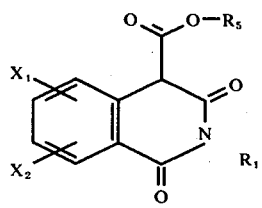

| R₁ | R₅ | X₁ | X₂ |
|---|---|---|---|
| o-hydroxyphenyl | ethyl | 6-methylsulfonyl | 7-chloro |
| benzyl | ethyl | hydrogen | 7-ethoxy |
| o-fluorobenzyl | ethyl | hydrogen | 7-fluoro |
| p-bromobenzyl | ethyl | hydrogen | 7-chloro |
| p-ethoxybenzyl | ethyl | hydrogen | 8-bromo |
| m-isopropylbenzyl | ethyl | hydrogen | 7-ethoxy |
| o-methylbenzyl | ethyl | hydrogen | 6-isopropyl |
| m-trifluoromethylbenzyl | ethyl | hydrogen | 6-trifluoromethyl |
| m-nitrobenzyl | ethyl | hydrogen | 5-nitro |
| p-aminobenzyl | ethyl | hydrogen | 6-amino |
| o-methylsulfonylbenzyl | ethyl | hydrogen | 7-methylsulfonyl |
| m-trifluoromethylsulfonylbenzyl | ethyl | hydrogen | 7-trifluoromethylsulfonyl |
| m-dimethylsulfonamidobenzyl | ethyl | hydrogen | 7-dimethylsulfonamido |
| p-acetamidobenzyl | ethyl | hydrogen | 6-acetamido |
| p-acetamidobenzyl | ethyl | hydrogen | 7-hydroxy |
| o-hydroxybenzyl | ethyl | hydrogen | 7-chloro |

EXAMPLE XLII

7-Methoxy-2-methyl-1,3(2H,4H)-dioxoisoquinoline-4-(N,N-tetramethylene)carboxamide A solution of ethyl 7-methoxy-2-methyl-1,3(2H,4H)-dioxoisoquinoline-4-carboxylate (6.9 g., 0.025 mole), prepared as in Example XL, and pyrrolidine (1.8 g., 0.026 mole) in 100 ml. of xylene is refluxed for four hours, during which time solvent is distilled off until the temperature of solvent vapors in the distilling head are within two degrees of the temperature of the reaction mixture. The volume of the reaction mixture is maintained by occasional addition of xylene. The mixture is then allowed to cool and the resulting crystals are collected by filtration, dried and recrystallized from acetonitrile to give the desired 7-methoxy-2-methyl-1,3(2H,4H)-isoquinoline-4-(N,N-tetramethylene)carboxamide.

EXAMPLE XLIII

The procedure of Example XLII is repeated, using equivalent amounts of appropriate substrates, to produce the following compounds:

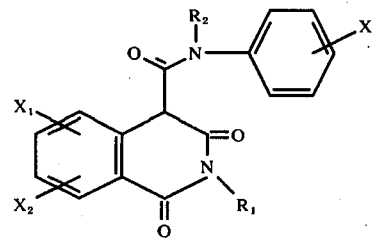

| R₁ | R₂ | X | X₁ | X₂ |
|---|---|---|---|---|
| H | H | 2',5'-diCl | hydrogen | 7-chloro |
| H | H | 3',4'-diCH₃ | 6-methoxy | 7-methoxy |
| H | H | 3',4'-diCl | hydrogen | 7-methoxy |
| H | H | 2',5'-diOCH₃ | 6-methoxy | hydrogen |
| CH₃ | CH₃ | H | 5-nitro | hydrogen |
| CH₃ | CH₃ | 4'-Cl | 6-fluoro | 8-propyl |
| CH₃ | H | 4'-Br | 5-nitro | 8-nitro |
| CH₃ | H | 4'-F | hydrogen | 7-amino |
| CH₃ | H | 4'-CF₃ | 6-chloro | 7-chloro |
| CH₃ | H | 2',3'-diCl | 6-methyl | 7-methyl |
| CH₃ | H | 2',4'-diCl | hydrogen | 7-chloro |
| CH₃ | H | 2'-COOC₂H₅ | 6-chloro | 7-chloro |
| CH₃ | H | 4'-COOC₂H₅ | 6-methylsulfonyl | 7-methylsulfonyl |
| CH₃ | H | 5'-Cl—2'-OCH₃ | hydrogen | 7-trifluoromethylsulfonyl |
| CH₃ | H | 3',5'-diCl | 5-methyl | 7-dimethylsulfonamido |
| CH₃ | H | 3',5'-diOCH₃ | 6-bromo | 8-acetamido |
| CH₃ | H | 2',6'-diCH₃ | 5-hydroxy | 8-hydroxy |
| CH₃ | H | 2'-OCH₃-5'-CH₃ | 6-fluoro | hydrogen |
| CH₃ | H | 2',4'-diCH₃ | hydrogen | 8-chloro |
| CH₃ | H | 2',5'-diCH₃ | 5-bromo | hydrogen |
| CH₃ | H | 3'-Cl—4'-CH₃ | 6-ethoxy | hydrogen |
| CH₃ | H | 3'-CO—CH₃ | hydrogen | 7-isopropyl |
| CH₃ | H | 3'-Cl—2'-CH₃ | hydrogen | 7-amino |

-continued

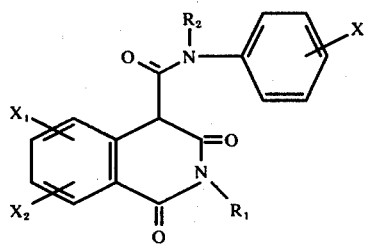

| R₁ | R₂ | X | X₁ | X₂ |
|---|---|---|---|---|
| CH₃ | H | 3',5'-diCH₃ | hydrogen | 7-trifluoromethyl |
| CH₃ | H | 2'-Cl—4'-CH₃ | 6-methylsulfonyl | 7-chloro |
| CH₃ | H | 2'-CH₃-4'-OCH₃ | hydrogen | 7-ethoxy |
| CH₃ | H | 4'-Cl—2'-CH₃ | hydrogen | 7-fluoro |
| CH₃ | H | 2'-Cl—5'-CF₃ | hydrogen | 7-chloro |
| H | H | 2',4'-diOCH₃ | hydrogen | 8-bromo |
| H | H | 4'-F | hydrogen | 7-ethoxy |
| H | H | 4'-CF₃ | hydrogen | 6-isopropyl |
| H | H | 4'-Br | hydrogen | 6-trifluoromethyl |

EXAMPLE XLIV

The procedure of Example XLII is repeated, using equivalent amounts of appropriate substrates, to produce the following compounds:

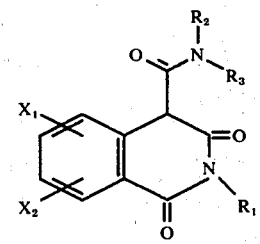

| R₁ | R₂ | R₃ | X₁ | X₂ |
|---|---|---|---|---|
| hexyl | ethoxyethyl | ethyl | hydrogen | 7-chloro |
| benzyloxy | hydrogen | 1,1-dimethyl-2-butynyl | 6-methoxy | 7-methoxy |
| methoxy | methoxyethyl | 3-acetylphenyl | hydrogen | 7-methoxy |
| hexyl | hydrogen | t-butyl | 6-methoxy | hydrogen |
| cyclopropyl | methyl | n-hexyl | 5-nitro | hydrogen |
| cyclohexyl | i-propyl | 3-hexenyl | 6-fluoro | 8-propyl |
| 2-furyl | n-hexyl | propargyl | 5-nitro | 8-nitro |
| 2-tetrahydrofuryl | allyl | cyclopropyl | hydrogen | 7-amino |
| furfuryl | 2,3-dimethyl-3-butenyl | trifluoromethyl | 6-chloro | 7-chloro |
| tetrahydrofurfuryl | hydrogen | hexafluoroisopropyl | 6-methyl | 7-methyl |
| ethyl | hydrogen | adamantyl | hydrogen | 7-chloro |
| p-bromophenyl | hydrogen | butynyl | 6-chloro | 7-chloro |
| p-ethoxyphenyl | ethyl | tetrahydrofurfuryl | 6-methylsulfonyl | 7-methylsulfonyl |
| m-isopropylphenyl | n-propyl | pyridyl | hydrogen | 7-trifluoromethylsulfonyl |
| o-methylphenyl | neopentyl | 3-fluoro-5-propylphenyl | 5-methyl | 7-dimethylsulfonamido |
| m-trifluoromethylphenyl | hydrogen | 2,5-dinitrophenyl | 6-bromo | 8-acetamido |
| m-nitrophenyl | methyl | 4-aminophenyl | 5-hydroxy | 8-hydroxy |
| p-aminophenyl | i-propyl | 3,5-bis-methylsulfonylphenyl | 6-fluoro | hydrogen |
| o-methylsulfonylphenyl | hydrogen | 4-trifluoromethylsulfonylphenyl | hydrogen | 8-chloro |
| m-trifluoromethylsulfonylphenyl | n-hexyl | 2-methyl-4-dimethylsulfonamidophenyl | 5-bromo | hydrogen |
| m-dimethylsulfonamidophenyl | allyl | 3-bromo-5-acetamidophenyl | 6-ethoxy | hydrogen |
| p-acetamidophenyl | 2,3-dimethyl-3-butenyl | 2,5-dihydroxyphenyl | hydrogen | 7-isopropyl |
| o-hydroxyphenyl | hydrogen | 2-fluoronaphthyl | hydrogen | 7-amino |

-continued

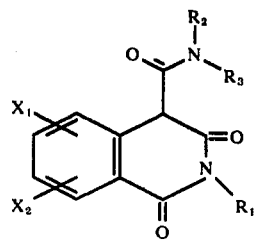

| R₁ | R₂ | R₃ | X₁ | X₂ |
| --- | --- | --- | --- | --- |
| o-fluorobenzyl | methyl | 3-chloronaphthyl | hydrogen | 7-trifluoromethyl |
| p-bromobenzyl | hydrogen | 4-bromonaphthyl | 6-methylsulfonyl | 7-chloro |
| p-ethoxybenzyl | ethyl | 5-ethoxynaphthyl | hydrogen | 7-ethoxy |
| m-isopropyl-o-benzyl | n-propyl | 5-isopropylnaphthyl | hydrogen | 7-fluoro |
| o-methylbenzyl | neopentyl | 5-trifluoromethylnaphthyl | hydrogen | 7-chloro |
| m-nitrobenzyl | methyl | 2-aminonaphthyl | hydrogen | 8-bromo |
| p-aminobenzyl | i-propyl | 5-methylsulfonylnaphthyl | hydrogen | 7-ethoxy |
| o-methylsulfonylbenzyl | hydrogen | 5-trifluoromethylsulfonylnaphthyl | hydrogen | 6-isopropyl |
| m-trifluoromethylsulfonylbenzyl | n-hexyl | 5-dimethylsulfonamidonaphthyl | hydrogen | 6-trifluoromethyl |
| m-dimethylsulfonamidobenzyl | allyl | 3-acetamidonaphthyl | hydrogen | 5-nitro |
| p-acetamidobenzyl | 2,3-dimethyl-3-butenyl | 4-hydroxynaphthyl | hydrogen | 6-amino |
| o-hydroxybenzyl | hydrogen | 2'-fluorobenzyl | hydrogen | 7-methylsulfonyl |
| hexyl | hydrogen | 3'-chlorobenzyl | hydrogen | 7-trifluoromethylsulfonyl |
| cyclopropyl | hydrogen | 4'-bromobenzyl | hydrogen | 7-dimethylsulfonamido |
| cyclohexyl | ethyl | 4'-ethoxybenzyl | hydrogen | 6-acetamido |
| propargyl | n-propyl | 3'-i-propylbenzyl | hydrogen | 7-hydroxy |
| 2-furyl | neopentyl | 2'-trifluoromethylbenzyl | hydrogen | 7-chloro |
| 2-tetrahydrofuryl | hydrogen | 4'-nitrobenzyl | hydrogen | 7-chloro |
| furfuryl | methyl | 2'-aminobenzyl | 6-methoxy | 7-methoxy |
| tetrahydrofurfuryl | i-propyl | 4'-methylsulfonylbenzyl | hydrogen | 7-methoxy |
| o-fluorophenyl | hydrogen | 4'-trifluoromethylsulfonylbenzyl | 6-methoxy | hydrogen |
| p-bromophenyl | n-hexyl | 3'-dimethylsulfonamidobenzyl | 5-nitro | hydrogen |
| p-ethoxyphenyl | allyl | 2'-acetamidobenzyl | 6-fluoro | 8-propyl |
| m-isopropylphenyl | 2,3-dimethyl-3-butenyl | 2'-hydroxybenzyl | 5-nitro | 8-nitro |
| o-methylphenyl | hydrogen | 2'-fluoro-β-phenethyl | hydrogen | 7-amino |
| m-trifluoromethylphenyl | 2-CH₃—3-butynyl | 3'-Cloro-β-phenethyl | 6-chloro | 7-chloro |
| m-nitrophenyl | hydrogen | 4'-Bromo-β-phenethyl | 6-methyl | 7-methyl |
| p-aminophenyl | ethyl | 4'-ethoxy-β-phenethyl | hydrogen | 7-chloro |
| o-methylsulfonylphenyl | n-propyl | 3'-i-propyl-β-phenethyl | 6-chloro | 7-chloro |
| m-trifluoromethylsulfonylphenyl | neopentyl | 2'-trifluoromethyl-β-phenethyl | 6-methylsulfonyl | 7-methylsulfonyl |
| m-dimethylsulfonamidophenyl | H | 4'-nitro-β-phenethyl | hydrogen | 7-trifluoromethylsulfonyl |
| p-acetamidophenyl | methyl | 2'-amino-β-phenethyl | 5-methyl | 7-dimethylsulfonamido |
| o-hydroxyphenyl | 1-propyl | 4'-methylsulfonyl-β-phenethyl | 6-bromo | 8-acetamido |
| o-fluorobenzyl | hydrogen | 4'-trifluoromethyl-β-phenethyl | 5-hydroxy | 8-hydroxy |
| p-bromobenzyl | n-hexyl | 3'-dimethylsulfonamido-β-phenethyl | 6-fluoro | hydrogen |
| p-ethoxybenzyl | allyl | 2'-acetamido-β-phenethyl | hydrogen | 8-chloro |
| m-isopropylbenzyl | 2,3-diCH₃—3-butenyl | 2'-hydroxy-β-phenethyl | 5-bromo | hydrogen |
| o-methylbenzyl | | hexamethyleneimine | 6-ethoxy | hydrogen |
| m-trifluoromethylbenzyl | | piperazine | hydrogen | 7-isopropyl |
| m-nitrobenzyl | | N-methylpiperazine | hydrogen | 7-amino |

-continued

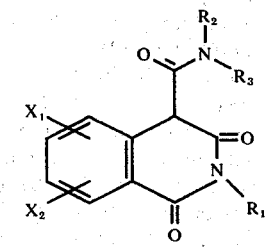

| R₁ | R₂ | R₃ | X₁ | X₂ |
|---|---|---|---|---|
| p-aminobenzyl | N-phenylpiperazine | | hydrogen | 7-trifluoromethyl |

EXAMPLE XLV

Each of the following 1,3(2H,4H)-dioxoisoquinoline-4-carboxamides were tested for anti-inflammatory activity using the carrageenin rat food edema test and were found to be active at the indicated dosage level:

| R₁ | R₃ | X₁ | X₂ | Dosage, mg/kg |
|---|---|---|---|---|
| methyl | phenyl | hydrogen | 7-chloro | 10 |
| methyl | ethyl | hydrogen | 7-chloro | 10 |
| methyl | ethyl | 6-methoxy | 7-methoxy | 100 |
| methyl | 4-chlorophenyl | 6-methoxy | 7-methoxy | 10 |
| methyl | phenyl | 6-methoxy | 7-methoxy | 100 |
| methyl | 4-methoxyphenyl | hydrogen | 7-methoxy | 33 |
| methyl | 4-chlorophenyl | hydrogen | 7-methoxy | 33 |
| methyl | phenyl | hydrogen | 7-methoxy | 100 |
| methyl | 2-methoxyphenyl | hydrogen | 7-methoxy | 100 |
| methyl | 2,5-dichlorophenyl | hydrogen | 7-methoxy | 33 |
| methyl | 2-methylphenyl | 6-methoxy | 7-methoxy | 100 |
| hydrogen | ethyl | 6-methoxy | 7-methoxy | 100 |
| hydrogen | phenyl | hydrogen | 7-chloro | 3.3 |
| hydrogen | 4-chlorophenyl | hydrogen | 7-chloro | 33 |
| hydrogen | ethyl | hydrogen | 7-chloro | 100 |
| hydrogen | phenyl | 6-methoxy | 7-methoxy | 200 |
| hydrogen | 4-chlorophenyl | hydrogen | 7-methoxy | 100 |
| hydrogen | 4-chlorophenyl | 6-methoxy | 7-methoxy | 200 |
| methyl | 2-chlorophenyl | hydrogen | 7-methoxy | 200 |
| methyl | 2-chlorophenyl | 6-methoxy | 7-methoxy | 200 |
| hydrogen | phenyl | hydrogen | 7-methoxy | 33 |

EXAMPLE XLVI 2-(m-Chlorophenyl)-5,6,7,8-tetrahydroisoquinoline-1,3(2H,4H)-dione A mixture of tetrahydrohomophthalic acid (46.0 g., 0.25 mole) and m-chloroaniline (31.8 g., 0.25 mole) is heated by an oil bath until molten for two hours. When removed from the oil bath, the reaction mixture solidifies and is recrystallized twice from ethanol/ethyl acetate, giving 2-(m-chlorophenyl)-5,6,7,8-tetrahydroisoquinoline-1,3(2H,4H)-dione.

EXAMPLE XLVII

2-Allyl-5,6,7,8-tetrahydroisoquinoline-1,3(2H,4H)-dione

A mixture of tetrahydrohomophthalic acid (9.2 g., 0.05 mole) and allylamine (2.8 g., 0.05 mole) is heated by an oil bath until molten for 40 minutes. The mixture solidifies upon cooling, and is recrystallized twice from isopropanol, giving 2-allyl-5,6,7,8-tetrahydroisoquinoline-1,3(2H,4H)-dione.

EXAMPLE XLVIII

2-Isopropyl-5,6,7,8-tetrahydroisoquinoline-1,3(2H,4H)-dione

A mixture of tetrahydrohomophthalic acid (92 g., 0.5 mole) and isopropylamine (59 g., 1 mole) is heated by an oil bath until molten for 90 minutes. The hot mixture is then poured into 600 ml. of ethanol, treated with carbon black and filtered. The mixture is concentrated to about 300 ml. and slowly cooled to room temperature. 2-Isopropylisoquinoline-1,3(2H,4H)-dione precipitates and is collected by filtration.

EXAMPLE IL

2-Methoxy-5,6,7,8-tetrahydroisoquinoline-1,3(2H,4H)-dione

A mixture of tetrahydrohomophthalic acid (9.2 g., 0.05 mole) and methoxyamine hydrochloride (4.25 g., 0.05 mole) in 125 ml. of xylene is refluxed for 90 minutes, with water collected in Dean Stark trap as it formed. The reaction mixture is cooled and concentrated by vacuum to one-half its original volume, then diluted with ethyl acetate, washed with water and dried over sodium sulfate. Recrystallization from isopropanol and ethanol, followed by drying at 100° C. for 4 hours yields 2-methoxy-5,6,7,8-tetrahydroisoquinoline-1,3(2H,4H)-dione.

EXAMPLE L

The following products are prepared by the procedure of Example XLVI by substituting an appropriate amine in place of said m-chloroaniline:

2-Hexyl-5,6,7,8-tetrahydroisoquinoline-1,3(2H,4H)-dione
2-Cyclopropyl-5,6,7,8-tetrahydroisoquinoline-1,3(2H,4H)-dione
2-Cyclohexyl-5,6,7,8-tetrahydroisoquinoline-1,3(2H,4H)-dione
2-Propargyl-5,6,7,8-tetrahydroisoquinoline-1,3(2H,4H)-dione 2-(2'-Furyl)-5,6,7,8-tetrahydroisoquinoline-1,3(2H,4H)-dione
2-(2'-Tetrahydrofuryl)-5,6,7,8-tetrahydroisoquinoline-1,3(2H,4H)-dione
2-Furfuryl-5,6,7,8-tetrahydroisoquinoline-1,3(2H,4H)-dione
2-Tetrahydrofurfuryl-5,6,7,8-tetrahydroisoquinoline-1,3(2H,4H)-dione
2-(o-Fluorophenyl)-5,6,7,8-tetrahydroisoquinoline-1,3(2H,4H)-dione
2-(p-Bromophenyl)-5,6,7,8-tetrahydroisoquinoline-1,3(2H,4H)-dione
2-(p-Ethoxyphenyl)-5,6,7,8-tetrahydroisoquinoline-1,3(2H,4H)-dione
2-(m-Isopropylphenyl)-5,6,7,8-tetrahydroisoquinoline-1,3(2H,4H)-dione
2-(o-Methylphenyl)-5,6,7,8-tetrahydroisoquinoline-1,3(2H,4H)-dione
2-(m-Trifluoromethylphenyl)-5,6,7,8-tetrahydroisoquinoline-1,3(2H,4H)-dione
2-(m-Nitrophenyl)-5,6,7,8-tetrahydroisoquinoline-1,3(2H,4H)-dione
2-(p-Aminophenyl)-5,6,7,8-tetrahydroisoquinoline-1,3(2H,4H)-dione
2-(o-Methylsulfonylphenyl)-5,6,7,8-tetrahydroisoquinoline-1,3(2H,4H)-dione
2-(m-Trifluoromethylsulfonylphenyl)-5,6,7,8-tetrahydroisoquinoline-1,3(2H,4H)-dione
2-(m-Dimethylsulfonamidophenyl)-5,6,7,8-tetrahydroisoquinoline-1,3(2H,4H)-dione
2-(p-Acetamidophenyl)-5,6,7,8-tetrahydroisoquinoline-1,3(2H,4H)-dione
2-(o-Hydroxyphenyl)-5,6,7,8-tetrahydroisoquinoline-1,3(2H,4H)-dione
2-(o-Fluorobenzyl)-5,6,7,8-tetrahydroisoquinoline-1,3(2H,4H)-dione
2-(p-Bromobenzyl)-5,6,7,8-tetrahydroisoquinoline-1,3(2H,4H)-dione
2-(p-Ethoxybenzyl)-5,6,7,8-tetrahydroisoquinoline-1,3(2H,4H)-dione
2-(m-Isopropylbenzyl)-5,6,7,8-tetrahydroisoquinoline-1,3(2H,4H)-dione
2-(o-Methylbenzyl)-5,6,7,8-tetrahydroisoquinoline-1,3(2H,4H)-dione
2-(m-Trifluoromethylbenzyl)-5,6,7,8-tetrahydroisoquinoline-1,3(2H,4H)-dione
2-(m-Nitrobenzyl)-5,6,7,8-tetrahydroisoquinoline-1,3(2H,4H)-dione
2-(p-Aminobenzyl)-5,6,7,8-tetrahydroisoquinoline-1,3(2H,4H)-dione
2-(o-Methylsulfonylbenzyl)-5,6,7,8-tetrahydroisoquinoline-1,3(2H,4H)-dione
2-(m-Trifluoromethylsulfonylbenzyl)-5,6,7,8-tetrahydroisoquinoline-1,3(2H,4H)-dione
2-(m-Dimethylsulfonamidobenzyl)-5,6,7,8-tetrahydroisoquinoline-1,3(2H,4H)-dione
2-(p-Acetamidobenzyl)-5,6,7,8-tetrahydroisoquinoline-1,3(2H,4H)-dione
2-(o-Hydroxybenzyl)-5,6,7,8-tetrahydroisoquinoline-1,3(2H,4H)-dione

EXAMPLE LI

2-Methyl-5,6,7,8-tetrahydro-1,3(2H,4H)-dioxoisoquinoline-4-carboxamide

A solution of potassium cyanate (2.84 g., 0.035 mole) in 10 ml. of water is added with stirring, over a 30 minute period, to a solution of 2-methyl-5,6,7,8-tetrahydro-1,3(2H,4H)-dioxoisoquinoline (4.5 g., 0.025 mole) in 20 ml. of dimethylformamide which has been heated over a steam bath. The resulting solution is heated for an additional two hours and then poured into an excess of ice water containing 10 ml. of 6N hydrochloric acid. The resulting precipitate is filtered, dried and recrystallized from acetonitrile to give 2-methyl-5,6,7,8-tetrahydro-1,3(2H,4H)-dioxoisoquinoline-4-carboxamide.

EXAMPLE LII

The procedure of Example LI is repeated, using products of Examples XLVI-IX in place of said 2-methyl-5,6,7,8-tetrahydro-1,3(2H,4H)-dioxoisoquinoline, to prepare the following compounds:

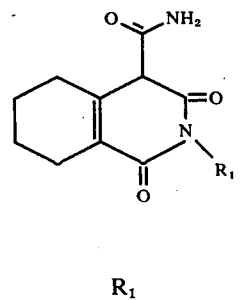

$R_1$ m-chlorophenyl
allyl
isopropyl
hexyl
cyclopropyl
cyclohexyl
propargyl
2'-furyl
2'-tetrahydrofuryl
furfuryl
tetrahydrofurfuryl
methoxy
hydroxy
benzyloxy
phenyl
o-fluorophenyl
p-bromophenyl
p-ethoxyphenyl
m-isopropylphenyl
o-methylphenyl
m-trifluoromethylphenyl
m-nitrophenyl
p-aminophenyl
o-methylsulfonylphenyl
m-trifluoromethylsulfonylphenyl
m-dimethylsulfonamidophenyl
p-acetamidophenyl o-hydroxyphenyl
benzyl
o-fluorobenzyl
p-bromobenzyl
p-ethoxybenzyl
m-isopropylbenzyl
o-methylbenzyl
m-trifluoromethylbenzyl
m-nitrobenzyl
p-aminobenzyl
o-methylsulfonylbenzyl
m-trifluoromethylsulfonylbenzyl
m-dimethylsulfonamidobenzyl
p-acetamidobenzyl
p-acetamidobenzyl
o-hydroxybenzyl

EXAMPLE LIII

2-Methyl-5,6,7,8-Tetrahydro-1,3(2H,4H)-dioxoisoquinoline-4-carboxanilide

A solution containing 2-methyl-5,6,7,8-tetrahydro-1,3(2H,4H)-dioxoisoquinoline (4.4 g., 0.025 mole), triethylamine (2.6 g., 0.026 mole) and phenylisocyanate (3.1 g., 0.026 mole) in 100 ml. of tetrahydrofuran was refluxed for 2 hours. The solution was then poured into an excess of ice water containing 5 ml. of hydrochloric acid. The resulting precipitate was collected by filtration, washed with water, dried and recrystallized from acetic acid, to give 2-methyl-5,6,7,8-tetrahydro-1,3(2H,4H)-dioxoisoquinoline-4-carboxanilide, m.p. 177°–178° C.

Anal. Calc'd for $C_{17}H_{18}N_2O_3$: C, 68.44; H, 6.08; N, 9.39. Found: C, 68.52; H, 6.09; N, 9.44.

EXAMPLE LIV

The procedure of Example LIII was repeated, using appropriately substituted substrates, to produce the following compounds:

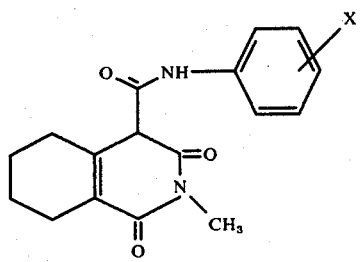

| X | M.p., °C. | Anal: Calc'd C | H | N | Found C | H | N |
|---|---|---|---|---|---|---|---|
| 2'-Cl | 196–197 (dec.) | 61.35 | 5.15 | 8.42 | 61.35 | 5.15 | 8.46 |
| 4'-Cl | 178–179 (dec.) | 61.35 | 5.15 | 8.42 | 61.37 | 5.20 | 8.64 |
| 2'-OCH$_3$ | 184–189 (dec.) | 65.84 | 6.14 | 8.53 | 65.76 | 6.05 | 8.54 |
| 4'-OCH$_3$ | 211–212 (dec.) | 65.84 | 6.14 | 8.53 | 66.09 | 6.22 | 8.56 |

EXAMPLE LV

The procedure of Example LIII is repeated, using appropriately substituted substrates to produce the following compounds:

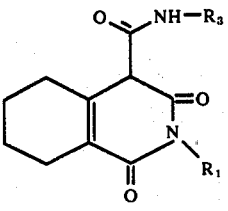

| R$_1$ | R$_3$ |
|---|---|
| neopentyl | acetyl |
| hydrogen | butyryl |
| phenyl | benzoyl |
| m-trifluoromethylbenzyl | 3-nitronaphthyl |
| methyl | n-butyl |
| m-chlorophenyl | benzoyl |
| methyl | carbethoxymethyl |
| methyl | phenyl |
| methyl | 2'-chlorophenyl |
| methyl | 3'-chlorophenyl |
| methyl | 4'-chlorophenyl |
| methyl | 2'-methoxyphenyl |
| methyl | 4'-methoxyphenyl |
| methyl | 2'-ethoxyphenyl |
| methyl | 4'-ethoxyphenyl |
| m-chlorophenyl | phenyl |
| benzyl | phenyl |
| allyl | phenyl |

EXAMPLE LVI

2-Methyl-5,6,7,8-tetrahydro-1,3(2H,4H)-dioxoisoquinoline-4-(2'-methyl)carboxanilide To a stirred mixture of 2-methyl-5,6,7,8-tetrahydro-1,3(2H,4H)-dioxoisoquinoline (4.4 g., 0.025 mole) and triethylamine (2.6 g., 0.026 mole) in 10 ml. of dimethylsulfoxide was added dropwise, over a five minute period, a solution of o-methylphenylisocyanate (3.5 g., 0.026 mole) in 10 ml of dimethylsulfoxide. After stirring for 2 hours, the solution was poured into an excess of ice water containing 5 ml. of hydrochloric acid. The resulting precipitate was collected by filtration, washed with water, dried and recrystallized from acetonitrile to give 2-methyl-5,6,7,8-tetrahydro-1,3(2H,4H)-dioxoisoquinoline-4-(2'-methyl)carboxanilide, m.p. 231° C. (dec.).

Anal. Calc'd for $C_{17}H_{18}N_2O_3$: C, 69.21; H, 6.45; N, 8.97. Found: C, 69.58; H, 6.58; N, 8.94.

EXAMPLE LVII

The procedure of Example LVI is repeated, using equivalent amounts of appropriate substrates, to produce the following compounds:

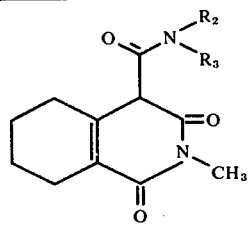

| R₁ | R₃ |
|---|---|
| hydrogen | methyl |
| hydrogen | ethyl |
| hydrogen | cyclohexyl |
| methyl | ethyl |
| methyl | n-propyl |
| methyl | cyclohexyl |
| methyl | methyl |
| m-chlorophenyl | ethyl |
| m-chlorophenyl | n-propyl |
| m-chlorophenyl | cyclohexyl |
| m-chlorophenyl | carbethoxymethyl |
| isopropyl | ethyl |
| allyl | ethyl |
| methyl | 2',5'-dichlorophenyl |
| hydrogen | 2'-chlorophenyl |
| hydrogen | 3'-chlorophenyl |
| hydrogen | 4'-chlorophenyl |
| hydrogen | 2'-methylphenyl |
| hydrogen | 3'-methylphenyl |
| hydrogen | 4'-methylphenyl |
| hydrogen | 2'-methoxyphenyl |
| hydrogen | 4'-methoxyphenyl |
| m-chlorophenyl | 2',5'-dichlorophenyl |
| hydrogen | 4'-ethoxyphenyl |
| hydrogen | 2'-ethoxyphenyl |

EXAMPLE LVIII

2-Methyl-5,6,7,8-tetrahydro-1,3(2H,4H)-dioxoisoquinoline-4-(N-benzyl)carboxamide A mixture of 2'-chloro-2-methyl-5,6,7,8-tetrahydro-1,3(2H,4H)-dioxoisoquinoline-4-carboxanilide (8.3 g., 0.025 mole), prepared by the procedure of Example LIV, and benzylamine (2.7 g., 0.025 mole) in 100 ml. of xylene is refluxed for 6 hours, after which time the mixture is allowed to cool. The resulting precipitate is collected by filtration, dried and recrystallized from xylene, giving 2-methyl-5,6,7,8-tetrahydro-1,3(2H,4H)-dioxo-2-methylisoquinoline-4-(N-benzyl)-carboxamide.

EXAMPLE LIX

The procedure of Example LVIII is repeated, using equivalent amounts of appropriate amines in place of said benzylamine, to produce the following compounds:

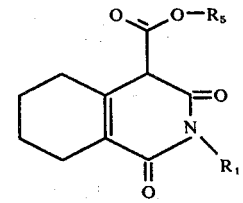

| R₂ | R₃ |
|---|---|
| —(CH₂)₅— | |
| —(CH₂)₂—O—2)₂— | |
| H | allyl |
| H | 4'—CH₃O—benzyl |
| H | 3',4'diCl—benzyl |
| H | β-phenethyl |
| H | 3',4'-diCH₃—phenyl |
| H | 3',4'-diCl—phenyl |
| H | 3'-CF₃—phenyl |
| H | 2',4'-diOCH₃—phenyl |
| H | 2',5'-diOCH₃—phenyl |

EXAMPLE LX

Ethyl 2-Methyl-5,6,7,8-tetrahydro-1,3(2H,4H)-dioxoisoquinoline-4-carboxylate

A mixture of 2'-chloro-2-methyl-5,6,7,8-tetrahydro-1,3(2H,4H)-dioxoisoquinoline-4-carboxanilide (16.7 g., 0.05 mole), prepared by the procedure of Example LIV, in 125 ml. of absolute ethanol is refluxed for 4 hours. The solution is then concentrated to one half its original volume and cooled slowly. The resulting precipitate is collected by filtration and dried to give ethyl 2-methyl-5,6,7,8-tetrahydro-1,3(2H,4H)-dioxoisoquinoline-4-carboxylate.

EXAMPLE LXI

The procedure of Example LX is repeated, using equivalent amounts of appropriately substituted carboxanilides and appropriate alcohol in place of said carbon-o-chloranilide and said ethanol, to produce the following compounds:

| R₁ | R₅ |
|---|---|
| hydrogen | ethyl |
| hexyl | methyl |
| cyclopropyl | methyl |
| cyclohexyl | methyl |
| propargyl | methyl |
| 2'-furyl | methyl |
| 2'-tetrahydrofurfuryl | i-propyl |
| furfuryl | i-propyl |
| tetrahydrofurfuryl | i-propyl |
| methoxy | i-propyl |
| hydroxy | i-propyl |
| benzyloxy | i-propyl |
| phenyl | i-propyl |
| o-fluorophenyl | i-propyl |
| p-bromophenyl | i-propyl |
| p-ethoxyphenyl | n-hexyl |
| m-isopropylphenyl | n-hexyl |
| o-methylphenyl | n-hexyl |

-continued

[Structure: tetrahydroisoquinoline-1,3-dione with COO-R₅ at position 4 and R₁ on N]

| R₁ | R₅ |
|---|---|
| m-trifluoromethylphenyl | n-hexyl |
| m-nitrophenyl | n-hexyl |
| p-aminophenyl | i-butyl |
| o-methylsulfonylphenyl | i-butyl |
| m-trifluoromethylsulfonylphenyl | i-butyl |
| m-dimethylsulfonamidophenyl | i-butyl |
| p-acetamidophenyl | i-butyl |
| o-hydroxyphenyl | ethyl |
| benzyl | ethyl |
| o-fluorobenzyl | ethyl |
| p-bromobenzyl | ethyl |
| p-ethoxybenzyl | ethyl |
| m-isopropylbenzyl | ethyl |
| o-methylbenzyl | ethyl |
| m-trifluoromethylbenzyl | ethyl |
| m-nitrobenzyl | ethyl |
| p-aminobenzyl | ethyl |
| o-methylsulfonylbenzyl | ethyl |
| m-trifluoromethylsulfonylbenzyl | ethyl |
| m-dimethylsulfonamidobenzyl | ethyl |
| p-acetamidobenzyl | ethyl |
| p-acetamidobenzyl | ethyl |
| o-hydroxybenzyl | ethyl |

EXAMPLE LXII

2-Methyl-5,6,7,8-tetrahydro-1,3(2H,4H)-dioxoisoquinoline-4-(N,N-tetramethylene)carboxamide A solution of ethyl 2-methyl-5,6,7,8-tetrahydro-1,3(2H,4H),dioxoisoquinoline-4-carboxylate (6.3 g., 0.025 mole) and pyrrolidine (1.8 g., 0.026 mole) in 100 ml. of xylene is refluxed for 4 hours, during which time solvent is distilled off until the temperature of solvent vapors in the distilling head is within two degrees of the temperature of the reaction mixture. The volume of the reaction mixture is maintained by occasional addition of xylene. The mixture is then allowed to cool, and the resulting crystals are collected by filtration, dried and recrystallized from acetonitrile to give 2-methyl-5,6,7,8-tetrahydro-1,3(2H,4H)-dioxoisoquinoline-4-(N,N-tetramethylene)carboxamide.

EXAMPLE LXIII

The procedure of Example LXII is repeated, using equivalent amounts of appropriate substrates, to produce the following compounds:

[Structure: tetrahydroisoquinoline-1,3-dione with C(O)N(R₂)(aryl-X) at position 4 and R₁ on N]

| R₁ | R₂ | X |
|---|---|---|
| H | H | 2',5'-diCl |
| H | H | 3',4'-diCH₃ |
| H | H | 3',4'-diCl |
| H | H | 2',5'-diOCH₃ |
| CH₃ | CH₃ | H |
| CH₃ | CH₃ | 4'-Cl |
| CH₃ | H | 4'-Br |
| CH₃ | H | 4'-F |
| CH₃ | H | 4'-CF₃ |
| CH₃ | H | 2',3'-diCl |
| CH₃ | H | 2',4'-diCl |
| CH₃ | H | 2'-COOC₂H₅ |
| CH₃ | H | 4'-COOC₂H₅ |
| CH₃ | H | 5'-Cl—2'-OCH₃ |
| CH₃ | H | 3',5'-diCl |
| CH₃ | H | 3',5'-diOCH₃ |
| CH₃ | H | 2',6'-diCH₃ |
| CH₃ | H | 2'-OCH₃—5'-CH₃ |
| CH₃ | H | 2',4'-diCH₃ |
| CH₃ | H | 2',5'-diCH₃ |
| CH₃ | H | 3'-Cl—4'-CH₃ |
| CH₃ | H | 3'-CO—CH₃ |
| CH₃ | H | 3'-Cl—2'-CH₃ |
| CH₃ | H | 3',5'-diCH₃ |
| CH₃ | H | 2'-Cl—4'-CH₃ |
| CH₃ | H | 2'-CH₃—4'-OCH₃ |
| CH₃ | H | 4'-Cl—2'-CH₃ |
| CH₃ | H | 2'-Cl—5'-CF₃ |
| H | H | 2',4'-diOCH₃ |
| H | H | 4'-F |
| H | H | 4'-CF₃ |
| H | H | 4'-Br |

EXAMPLE LXIV

The procedure of Example LXII is repeated, using equivalent amounts of appropriate substrates, to produce the following compounds:

[Structure: tetrahydroisoquinoline-1,3-dione with C(O)N(R₂)(R₃) at position 4 and R₁ on N]

| R₁ | R₂ | R₃ |
|---|---|---|
| hexyl | ethoxyethyl | ethyl |
| benzyloxy | hydrogen | 1,1-dimethyl-2-butynyl |
| methoxy | methoxyethyl | 3-acetylphenyl |
| hexyl | hydrogen | t-butyl |
| cyclopropyl | methyl | n-hexyl |
| cyclohexyl | i-propyl | 3-hexenyl |
| 2-furyl | n-hexyl | propargyl |
| 2-tetrahydrofuryl | allyl | cyclopropyl |
| furfuryl | 2,3-dimethyl-3-butenyl | trifluoromethyl |
| tetrahydrofurfuryl | hydrogen | hexafluoroisopropyl |

-continued

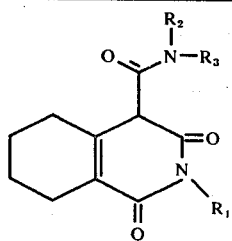

| R₁ | R₂ | R₃ |
|---|---|---|
| ethyl | hydrogen | adamantyl |
| p-bromophenyl | hydrogen | butynyl |
| p-ethoxyphenyl | ethyl | tetrahydrofurfuryl |
| m-isopropylphenyl | n-propyl | pyridyl |
| o-methylphenyl | neopentyl | 3-fluoro-5-propylphenyl |
| m-trifluoromethylphenyl | hydrogen | 2,5-dinitrophenyl |
| p-aminophenyl | i-propyl | 3,5-bis-methylsulfonyl-phenyl |
| o-methylsulfonylphenyl | hydrogen | 4-trifluoromethylsulfonyl-phenyl |
| m-trifluoromethylsulfonyl-phenyl | n-hexyl | 2-methyl-4-dimethylsul-fonamidophenyl |
| m-dimethylsulfonamidophenyl | allyl | 3-bromo-5-acetamido-phenyl |
| p-acetamidophenyl | 2,3-dimethyl-3-butenyl | 2,5-dihydroxyphenyl |
| o-hydroxyphenyl | hydrogen | 2-fluoronaphthyl |
| o-fluorobenzyl | methyl | 3-chloronaphthyl |
| p-bromobenzyl | hydrogen | 4-bromonaphthyl |
| p-ethoxybenzyl | ethyl | 5-ethoxynaphthyl |
| m-isopropylbenzyl | n-propyl | 5-isopropylnaphthyl |
| o-methylbenzyl | neopentyl | 5-trifluoromethyl-naphthyl |
| m-nitrobenzyl | methyl | 2-aminonaphthyl |
| p-aminobenzyl | i-propyl | 5-methylsulfonyl-naphthyl |
| o-methylsulfonylbenzyl | hydrogen | 5-trifluoromethylsul-fonylnaphthyl |
| m-trifluoromethylsulfonyl-benzyl | n-hexyl | 5-dimethylsulfonamido-naphthyl |
| m-dimethylsulfonamidobenzyl | allyl | 3-acetamidonaphthyl |
| p-acetamidobenzyl | 2,3-dimethyl-3-butenyl | 4-hydroxynaphthyl |
| o-hydroxybenzyl | hydrogen | 2'-fluorobenzyl |
| hexyl | hydrogen | 3'-chlorobenzyl |
| cyclopropyl | hydrogen | 4'-bromobenzyl |
| cyclohexyl | ethyl | 4'-ethoxybenzyl |
| propargyl | n-propyl | 3'-i-propylbenzyl |
| 2-furyl | neopentyl | 2'-trifluoromethylbenzyl |
| 2-tetrahydrofuryl | hydrogen | 4'-nitrobenzyl |
| furfuryl | methyl | 2'-aminobenzyl |
| tetrahydrofurfuryl | i-propyl | 4'-methylsulfonylbenzyl |
| o-fluorophenyl | hydrogen | 4'-trifluoromethylsul-fonylbenzyl |
| p-bromophenyl | n-hexyl | 3'-dimethylsulfonamido-benzyl |
| p-ethoxyphenyl | allyl | 2'-acetamidobenzyl |
| m-isopropylphenyl | 2,3-dimethyl-3-butenyl | 2'-hydroxybenzyl |
| o-methylphenyl | hydrogen | 2'-fluoro-β-phenethyl |
| m-trifluoromethylphenyl | 2-CH₃—3-butynyl | 3'-Chloro-β-phenethyl |
| m-nitrophenyl | hydrogen | 4'-Bromo-β-phenethyl |
| p-aminophenyl | ethyl | 4'-ethoxy-β-phenethyl |
| o-methylsulfonylphenyl | n-propyl | 3'-i-propyl-β-phenethyl |
| m-trifluoromethylsulfonyl-phenyl | neopentyl | 2'-trifluoromethyl-β-phenethyl |
| m-dimethylsulfonamidophenyl | H | 4'-nitro-β-phenethyl |
| p-acetamidophenyl | methyl | 2'-amino-β-phenethyl |
| o-hydroxyphenyl | i-propyl | 4'-methylsulfonyl-β-phenethyl |
| o-fluorobenzyl | hydrogen | 4'-trifluoromethyl-β-phenethyl |
| p-bromobenzyl | n-hexyl | 3'-dimethylsulfonamido-β-phenethyl |
| p-ethoxybenzyl | allyl | 2'-acetamido-β-phenethyl |
| m-isopropylbenzyl | 2,3-diCH₃—3-butenyl | 2'-hydroxy-β-phenethyl |
| o-methylbenzyl | | hexamethyleneimine |
| m-trifluoromethylbenzyl | | piperazine |
| m-nitrobenzyl | | N-methylpiperazine |
| p-aminobenzyl | | N-phenylpiperazine |

EXAMPLE LXV

Each of the following 5,6,7,8-tetrahydro-1,3(2H,4H)-dioxoisoquinoline-4-carboxamides were tested for anti-inflammatory activity using the rat foot edema test and were found to be active at the indicated dosage level:

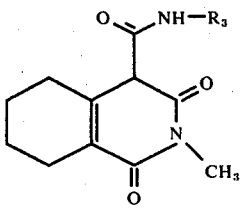

| $R_3$ | Dosage, mg/kg |
|---|---|
| phenyl | 33 |
| 2-chlorophenyl | 100 |
| 4-chlorophenyl | 33 |
| 2-methoxyphenyl | 33 |
| 4-methoxyphenyl | 33 |
| 2-methylphenyl | 33 |

EXAMPLE LXVI

Tablets

A tablet base is prepared by blending the following ingredients in the proportion by weight indicated:

| Maize starch | 20.0 |
|---|---|
| Dibasic calcium phosphate | 74.0 |
| Alginic acid | 16.0 |

Into this tablet base is blended sufficient 2-methyl-1,3(2H,4H)-dioxoisoquinoline-4-carboxanilide to provide tablets containing 20, 100 and 250 mg. of active ingredient per tablet. The compositions are compressed into tablets, each weighing 360 mg., by conventional means.

EXAMPLE LXVII

Capsules

A blend is prepared containing the following ingredients in the proportion by weight indicated:

| Maize starch | 100 |
|---|---|
| Sodium lauryl sulfate | 3.5 |

To this blend is added sufficient 4'; -chloro-1,3(2H,4H)-dioxoisoquinoline-4-carboxanilide to provide capsules containing 20, 100 and 250 mg. of active ingredient per capsule. The compositions are filled into conventional hard gelatin capsules in the amount of 350 mg. per capsule.

EXAMPLE LXVIII

Suspension

A suspension is prepared with the following composition

| 70% aqueous sorbitol | 741 g. |
|---|---|
| Glycerine, U.S.P. | 185 g. |
| Gum acacia (10% solution) | 100 ml. |
| Polyvinylpyrrolidone | 0.5 g. |
| Distilled water | Sufficient to make 1 liter | to which is added sufficient 2',4'-dichloro-2-methyl-1,3(2H,4H)-dioxoisoquinoline-4-carboxanilide to provide a concentration of approximately 25 mg. of active ingredient per milliliter. To this suspension, various sweeteners and flavorants may be added for the purpose of improving palatability.

What is claimed is:

1. A method for alleviating inflammation in the treatment of a subject afflicted with an inflammatory disorder which comprises administering to said subject an effective amount of a compound of the formula

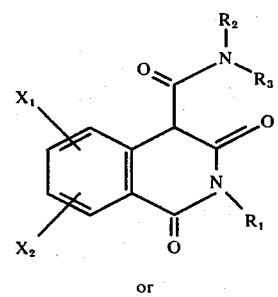

or

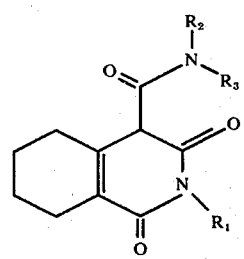

wherein:

$R_1$ is selected from the group consisting of hydrogen; alkyl having from 1 to 6 carbon atoms; alkyl phenyl with up to one substituent selected from the group consisting of fluorine, chlorine, bromine, methoxy, ethoxy and alkyl having up to 3 carbon atoms; and benzyl with up to 1 nuclear substituent selected from the group consisting of fluorine, chlorine, bromine, methoxy, ethoxy and alkyl having up to 3 carbon atoms;

$R_2$ is selected from the group consisting of hydrogen; primary alkyl having from 1 to 6 carbon atoms;

$R_3$ is selected from the group consisting of hydrogen; alkyl having from 1 to 6 carbon atoms, allyl; cycloalkyl having from 3 to 6 carbon atoms; polyfluoroalkyl having up to 3 carbon atoms; phenyl having up to 2 substituents each identically selected from the group consisting of fluorine, chlorine, bromine, methoxy, ethoxy, alkyl having up to 3 carbon atoms, acetyl and trifluoromethyl, or having 2 substituents each separately selected from the group consisting of chlorine, methyl, methoxy and trifluoromethyl; naphthyl and phenylalkyl having up to 2 carbon atoms in the alkyl moiety with up to 1 nuclear substituent selected from the group consisting of fluorine, chlorine, bromine, methoxy, ethoxy and alkyl having up to 3 carbon atoms; and $R_2$ and $R_3$, taken together, form a heterocycle selected from the group consisting of pyrrolidine, piperidine, hexamethyleneimine and morpholine;

provided that $R_2$ always is hydrogen when $R_3$ is tertiary alkyl; and $X_1$ and $X_2$ are at the 6 and 7 positions respectively are each identically selected from the group consisting of hydrogen, fluorine, chlorine, bromine, methoxy, ethoxy and alkyl having up to 3 carbon atoms and trifluoromethyl or either $X_1$ or $X_2$ is H and the other is as defined above.

2. The method as claimed in claim 1 wherein the compound administered has the formula

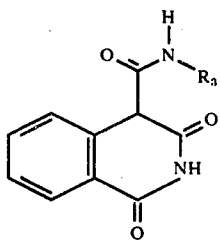

wherein $R_3$ is phenyl with up to 2 substituents each identically selected from the group consisting of fluorine, chlorine, bromine, alkoxy having up to 2 carbon atoms, alkyl having up to 3 carbon atoms, acetyl and trifluoromethyl, or having 2 substituents each separately selected from the group consisting of chlorine, methyl, methoxy and trifluoromethyl.

3. The method as claimed in claim 1 wherein the compound administered has the formula

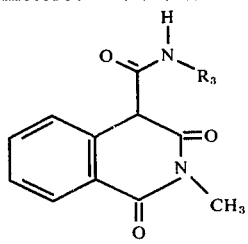

wherein $R_3$ is phenyl with up to 2 substituents each identically selected from the group consisting of fluorine, chlorine, bromine, alkoxy having up to 2 carbon atoms, alkyl having up to 3 carbon atoms, acetyl and trifluoromethyl, or having 2 substituents each separately selected from the group consisting of chlorine, methyl, methoxy and trifluoromethyl.

4. The method as claimed in claim 1 wherein the compound administered is 2-methyl-1,3(2H,4H)-dioxoisoquinoline-4-carboxanilide.

5. The method as claimed in claim 1 wherein the compound administered is 4'-chloro-2-methyl-1,3(2H,4H)-dioxoisoquinoline-4-carboxanilide.

6. The method as claimed in claim 1 wherein the compound administered is 4'-chloro-1,3(2H,4H)-dioxoisoquinoline-4-carboxanilide.

7. The method as claimed in claim 1 wherein the compound administered is 4'-fluoro-2-methyl-1,3(2H,4H)-dioxoisoquinoline-4-carboxanilide.

8. The method as claimed in claim 1, wherein the compound administered is 2',4'-dichloro-2-methyl-1,3(2H,4H)-dioxoisoquinoline-4-carboxanilide.

* * * * *